United States Patent
Tal

(10) Patent No.: US 12,279,785 B2
(45) Date of Patent: Apr. 22, 2025

(54) VASCULAR ACCESS LINE AND IMPLANTATION DEVICES AND METHODS

(71) Applicant: TACC INC, Wilmington, DE (US)

(72) Inventor: Michael Gabriel Tal, Tel Aviv (IL)

(73) Assignee: TACC INC., Wilmington, DE (US)

( * ) Notice: Subject to any disclaimer, the term of this patent is extended or adjusted under 35 U.S.C. 154(b) by 0 days.

(21) Appl. No.: 18/745,135

(22) Filed: Jun. 17, 2024

(65) Prior Publication Data

US 2024/0335209 A1     Oct. 10, 2024

Related U.S. Application Data

(63) Continuation of application No. PCT/US2023/010056, filed on Jan. 3, 2023.
(Continued)

(51) Int. Cl.
*A61B 17/32*     (2006.01)

(52) U.S. Cl.
CPC .. *A61B 17/32* (2013.01); *A61B 2017/320056* (2013.01)

(58) Field of Classification Search
CPC .. A61B 2017/03468; A61B 2017/0474; A61B 17/0482; A61B 17/0483; A61B 17/32; A61B 2017/320056; A61B 2017/22094; A61B 2017/00349; A61B 2017/22095; A61M 25/0169; A61M 2025/0175; A61M 25/0172; A61M 2025/0177; A61M 2025/018;
(Continued)

(56) References Cited

U.S. PATENT DOCUMENTS

| 5,439,467 A | 8/1995 | Benderev et al. |
| 5,499,991 A | 3/1996 | Garman et al. |

(Continued)

FOREIGN PATENT DOCUMENTS

WO     2006023975 A2     3/2006

OTHER PUBLICATIONS

International Preliminary Report on Patentability mailed on Mar. 27, 2024 in PCT/US2023/010056.
(Continued)

*Primary Examiner* — Shaun L David
*Assistant Examiner* — Rachael L Geiger
(74) *Attorney, Agent, or Firm* — Veros Legal Solutions, LLP

(57) ABSTRACT

Disclosed are a surgical tunneler, kits comprising the surgical tunneler, and methods of use thereof, for implanting access lines. The surgical tunneler includes a rigid elongated body, a rounded or pointed distal tip configured to dissect between tissue layers and/or to form a surgical tunnel when pushed subcutaneously in the body, and a guidewire capturing portion provided proximally to the distal tip. The guidewire capturing portion is configured to capture and/or fasten onto a target portion of an elastic stiff guidewire from within a body of a subject, such that the guidewire can be drawn with the surgical tunneler by way of pulling from the target portion thereof. In some embodiments, the surgical tunneler is capable of locally manipulating, folding and/or fixedly deforming a chosen portion of the elastic stiff guidewire, when guidewire capturing portion fasten onto the target portion.

34 Claims, 19 Drawing Sheets

Related U.S. Application Data

(60) Provisional application No. 63/395,155, filed on Aug. 4, 2022, provisional application No. 63/296,342, filed on Jan. 4, 2022.

(58) Field of Classification Search
CPC .. A61M 2025/0183; A61M 2025/0186; A61M 2025/0188; A61M 2025/0191; A61M 2025/0197; A61M 25/0194; A61M 25/09041; A61M 2025/09116; A61M 2025/09125; A61M 25/06; A61M 25/09; A61M 25/0082; A61M 25/0068; A61M 25/01
See application file for complete search history.

(56) References Cited

U.S. PATENT DOCUMENTS

| | | |
|---|---|---|
| 5,910,148 A | 6/1999 | Reimels et al. |
| 6,517,552 B1 | 2/2003 | Nord et al. |
| 6,716,228 B2 | 4/2004 | Tal |
| 6,770,084 B1 | 8/2004 | Bain et al. |
| 6,994,693 B2 | 2/2006 | Tal |
| 7,097,635 B2 | 8/2006 | McGuckin, Jr. et al. |
| 7,390,322 B2 | 6/2008 | McGuckin, Jr. et al. |
| 8,172,801 B2 | 5/2012 | Adams |
| 8,602,965 B2 | 12/2013 | Chu et al. |
| 8,702,625 B2 | 4/2014 | Ayala et al. |
| 9,913,962 B2 | 3/2018 | Tal et al. |
| 10,384,039 B2 | 8/2019 | Ribelin et al. |
| 2005/0149061 A1 | 7/2005 | Brassel |
| 2005/0154344 A1* | 7/2005 | Chang .............. A61B 17/12045 604/8 |
| 2008/0064988 A1 | 3/2008 | Carter et al. |
| 2008/0086114 A1* | 4/2008 | Schmitz ................ A61M 25/09 606/1 |
| 2019/0365364 A1* | 12/2019 | Chin ...................... A61B 34/30 |
| 2020/0282187 A1* | 9/2020 | Tay ................. A61M 25/09041 |
| 2022/0401706 A1 | 12/2022 | Tal |

OTHER PUBLICATIONS

International Search Report and Written Opinion in PCT/US2023/010056 dated Mar. 27, 2023.

\* cited by examiner

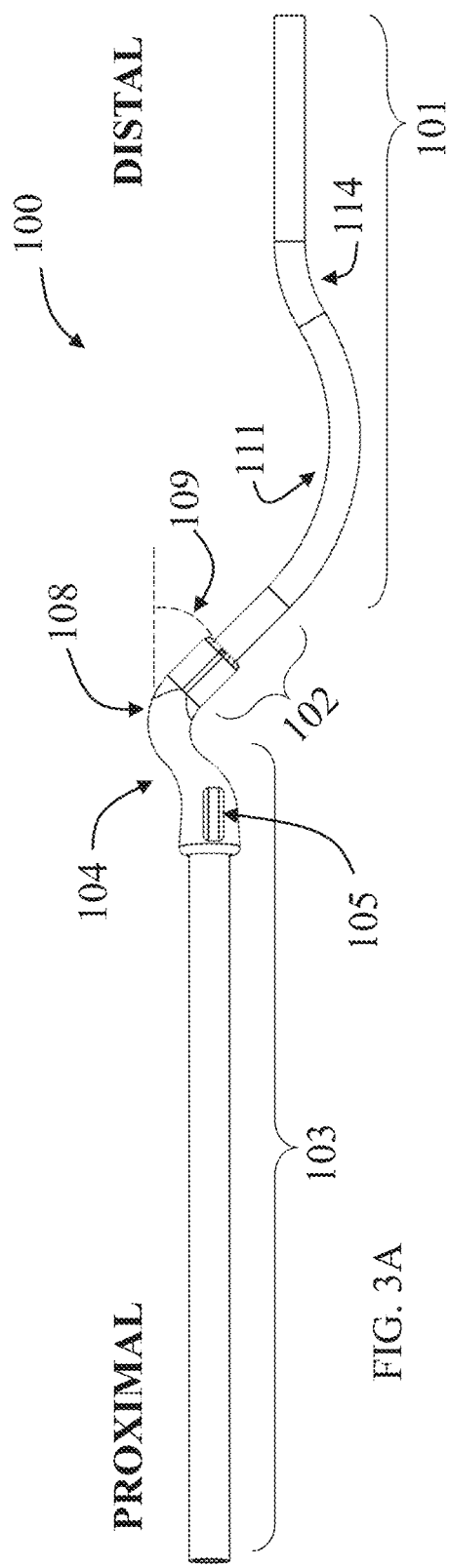
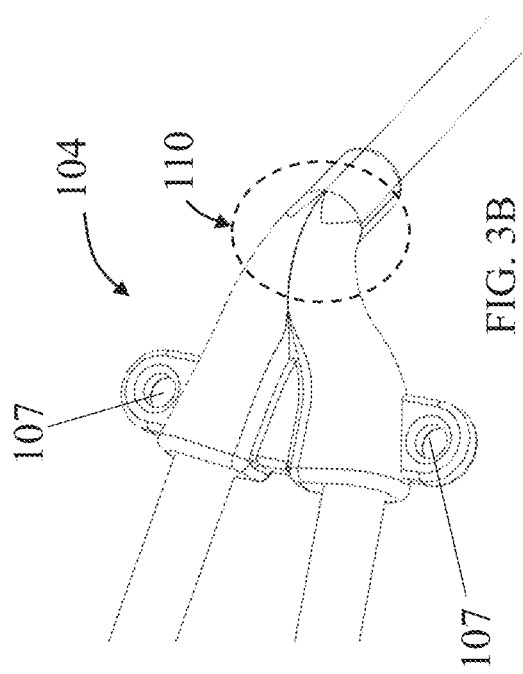
FIG. 3A
FIG. 3B (I)

(II)

(I)

(II)

(I)

(II)

VASCULAR ACCESS LINE AND IMPLANTATION DEVICES AND METHODS

RELATED APPLICATIONS

This application claims priority to PCT Application PCT/US2023/010056, filed on Jan. 3, 2023, which application claims priority to U.S. Provisional Patent Application No. 63/296,342, filed on Jan. 4, 2022, and to U.S. Provisional Patent Application No. 63/395,155, filed on Aug. 4, 2022; the entire contents of each of which are hereby incorporated by reference herein.

FIELD OF THE INVENTION

The present disclosure relates to vascular access lines and apparatus and methods for implanting vascular access lines, and more particularly, but not exclusively, to kits, devices and methods for implanting access lines through surgical tunnels.

BACKGROUND OF THE INVENTION

Vascular access complications are common, with thrombosis and infection being the two major ones. Thrombosis commonly follows clot formation around the implanted catheter, which often occludes the blood vessel, propagates centrally and causes pain and swelling due to inadequate venous drainage. Infections in vascular access are associated with mortality and morbidity in hospitals worldwide. Catheter related bloodstream infection (CRBSI) can be caused by bacteria propagating on the catheter and dislodging into the bloodstream causing disseminated infection or even sepsis.

One of the major causes of clotting with catheters is reduced blood flow rate following catheter implantation, whereas the smaller the vessel, the slower the flow around the catheter relative to normal flow rates prior to catheter implantation. The relation between the diameter of the vessel and the size of the catheter is a critical factor to consider for reducing the risk of clotting.

One of the common mechanisms of infection is passage of bacteria from the skin alongside the catheter from the skin entry site to the blood vessel. The greater the distance between the catheter entry site into the body and the blood vessel, the smaller the risk of infection is. For that reason, tunneled lines are known to reduce the risk of infections. Yet most lines, especially peripherally inserted central catheters (PICC) are inserted non tunneled. The reason is that a tunneled procedure is more complex to perform and involves two skin incisions, which increase risk for bleeding and infection and necessitates an operating room or an angiography suite.

Peripherally inserted central catheter (PICC) is a type of central venous catheter used for long-term intravenous access to the large central veins near the heart for antibiotics, chemotherapy, nutrition or medications, and for draw blood samples. PICC failure can occur due to infectious, mechanical or vascular complications including damage to veins, deep venous thrombosis (DVT), occlusion, catheter-associated blood stream infection (CABSI).

SUMMARY OF THE INVENTION

The present disclosure relates to devices and methods for implanting access lines such as catheters, and more particularly, but not exclusively, to kits, devices and methods for implanting access lines through surgical tunnels.

In certain embodiments, there is provided a surgical tunneler. The surgical tunneler may include a rigid elongated body, a rounded or pointed distal tip configured to dissect between tissue layers and/or to form a surgical tunnel when pushed subcutaneously in the body, and a guidewire capturing portion provided proximally to the distal tip. The guidewire capturing portion is configured to capture and fasten onto a target portion of an elastic stiff guidewire from within a body of a subject, such that the guidewire can be drawn with the surgical tunneler by way of pulling from the target portion thereof. In some embodiments, the surgical tunneler is capable of locally manipulating, folding and/or fixedly deforming a chosen portion of the elastic stiff guidewire, when guidewire capturing portion fasten onto the target portion.

In some embodiments, the surgical tunneler further comprising a tubular member selectively slidable axially over the elongated body, between a distal-most position wherein the tubular member covers the guidewire capturing portion and a proximal-most position wherein the guidewire capturing portion is fully uncovered for allowing capturing of the target portion therewith.

In some embodiments, the surgical tunneler is configured such that, when the guidewire capturing portion captures the target portion, the tubular member is selectively shiftable distally from the proximal-most position until causing the guidewire capturing portion to fasten onto the target portion.

In some embodiments, the surgical tunneler is configured such that, when the guidewire capturing portion captures the target portion, the tubular member is selectively shiftable distally from the proximal-most position until engaging with and causing the guidewire to fixedly deform sufficiently to form a local deviated portion, at or adjacent to the target portion, having smaller resistance to bending or folding relative to portions of the guidewire adjacent thereto.

In some embodiments, the surgical tunneler comprising a guidewire deforming mechanism comprising an anvil portion and a pressing portion selectively movable one against the other and configured to press the guidewire therebetween to a chosen shape for fixedly deforming the guidewire and/or forming a local deviated portion.

In some embodiments, the surgical tunneler comprising a clip mechanism incorporating the guidewire capturing portion, the clip mechanism includes a pair of opposing surfaces configured to capture and/or fasten onto the target portion therebetween.

In some embodiments, the clip mechanism comprising a jaw portion extending with a free end thereof between the elongated body and the distal tip, in juxtaposition with a stationary portion extending from the elongated body to the distal tip, wherein the pair of opposing surfaces is formed by and between the jaw portion and the stationary portion.

In some embodiments, the jaw portion emerges and protrudes distally from the elongated body with the free end thereof pointing towards the distal tip, so as to facilitate capturing of the target portion by pushing pair of opposing surfaces distally against the target portion.

In some embodiments, the stationary portion merges to the distal tip with a sloped surface configured for facilitating unhindered sliding of the target portion towards the clip mechanism.

In some embodiments, the clip mechanism is configured to form a gap between the pair of opposing surfaces sized for allowing sliding and/or capturing of the target portion therebetween.

In some embodiments, the surgical tunneler further comprising a tubular member selectively slidable axially over the clip mechanism, thereby forcing the pair of opposing surfaces to approximate for fasten onto the target portion.

In some embodiments, the clip mechanism, when in an elastically relaxed configuration, is configured to form a gap between the pair of opposing surfaces smaller than a thickness of the target portion, such that the target portion forces the pair of opposing surfaces to widen the gap when captured therebetween.

In some embodiments, the pair of surfaces are serrated.

In some embodiments, the guidewire capturing portion is configured as a carabiner comprising an elastically swingable gate shiftable laterally from a closed state towards a recess formed in the elongated body, when the gate is pressed against the target portion, and to elastically swing back to the closed state when the target portion extends through the recess and disengages from the gate.

In some embodiments, the surgical tunneler comprising a tissue cutting portion extending adjacent and/or parallel to the guidewire capturing carabiner, configured to cut through soft tissue between the guidewire capturing carabiner and the target portion.

In some embodiments, the tissue cutting portion includes a blade and/or cutting teeth.

In some embodiments, the tissue cutting portion extend along a length of the gate.

In some embodiments, the elongated body is shapeable to a fixed chosen contour.

In certain embodiments, there is provided a kit, comprising the surgical tunneler and at least one of a guidewire, an introducer and a vascular access line.

A kit according to claim 18, wherein the introducer comprising a splitable sheath placed over a dilator, configured to pass over the guidewire and to allow passing of the vascular access line therethrough.

In some embodiments, the vascular access line comprising a distal portion configured for placement in a blood vessel in a body of a subject, an intermediate portion configured to pass through a surgical opening and extend across skin layers in the body, a proximal portion configured to reside outside the body, and an elevating member fixedly attachable to the body. The elevating member comprising an elevated channel provided at a chosen height relative to a bottom surface of the elevating member. In some embodiments, the elevating member is configured to accommodate and/or hold the proximal portion within the elevated channel in a chosen shaped route above the bottom surface, when the elevating member is fixedly attached to the body, such that the intermediate portion is fixed at a chosen angle relative to the bottom surface and/or the blood vessel when in elastically relaxed state.

In some embodiments, the shaped route is curved and comprising an apex pointing away from or towards the bottom surface.

In some embodiments, the elevating member is attachable to the body by way of adhesion and/or suturing to an outer skin surface of the body.

In some embodiments, the elevating member is configured as a catheter hub and is fixedly connected to the proximal portion such as by way of overmolding.

In some embodiments, the elevating member is releasably or permanently connectable to a catheter hub fixedly connected to and/or molded over the proximal portion.

In some embodiments, the chosen angle is within a range of 20° to 90°, optionally about 45°.

In some embodiments, the vascular access line comprising two juxtaposing lumens, wherein the proximal portion includes a merging section, wherein the two juxtaposing lumens are divided between two distinct bodies extending proximally to the merging section, and divided by a wall in a unitary body extending distally to the merging section.

In some embodiments, the distal portion includes a first bent or curved section configured with a first radius of curvature and a first curve length when in an elastically relaxed state.

In some embodiments, the first bent or curved section is bent or curved upwards towards a plane coinciding with the bottom surface.

In some embodiments, the distal portion includes a second bent or curved section configured with a second radius of curvature and a second curve length when in an elastically relaxed state.

In some embodiments, the second bent or curved section is bent or curved downwards away from a plane coinciding with the bottom surface.

In certain embodiments, there is provided a method comprising: extending a guidewire along a preliminary insertion route within the body, between a first location on a skin of the subject and a bodily lumen, wherein a proximal end of the guidewire is outside the body and a distal end of the guidewire is inside the bodily lumen; capturing a target portion of the guidewire inside the body with the surgical tunneler; pulling the target portion to a second location on the skin, remote from the first location, wherein the guidewire follows a final insertion route within the body between the second location and the bodily lumen; and implanting the access line along the final insertion route.

In some embodiments, the capturing follows forming a surgical tunnel by advancing the surgical tunneler from the second location towards the target portion of the guidewire, wherein the pulling includes passing the target portion through the surgical tunnel towards and/or through the second opening.

In some embodiments, the method comprising fixedly deforming the guidewire using the surgical tunneler to form a local deviated portion at or adjacent to the target portion having reduced resistance to bending or folding relative to portions of the guidewire adjacent thereto.

In some embodiments, the final insertion route is substantially greater in length and/or inclined more gradually relatively to surface of the skin, than the preliminary insertion route.

In some embodiments, the capturing includes engaging the target portion with the guidewire capturing portion and pushing the surgical tunneler distally against the target portion for capturing the target portion with the guidewire capturing portion.

In some embodiments, the pulling includes releasing of bodily tissues from the guidewire capturing portion while holding the target portion with the guidewire capturing portion.

In some embodiments, the capturing is followed by fastening the guidewire capturing portion onto the target portion In certain embodiments, there is provided a vascular access line. The vascular access line may include a distal portion configured for placement in a blood vessel in a body of a subject, an intermediate portion configured to pass through a surgical opening and extend across skin layers in the body, a proximal portion configured to reside outside the body, and an elevating member fixedly attachable to the body, comprising an elevated channel provided at a chosen height relative to a bottom surface of the elevating member.

In some embodiments, the elevating member is configured to accommodate and/or hold the proximal portion within the elevated channel in a chosen shaped route above the bottom surface, when the elevating member is fixedly attached to the body, such that the intermediate portion is fixed at a chosen angle relative to the bottom surface and/or the blood vessel when in elastically relaxed state.

In some embodiments, the shaped route is curved and comprising an apex pointing away from or towards the bottom surface.

In some embodiments, wherein the elevating member is attachable to the body by way of adhesion and/or suturing to an outer skin surface of the body.

In some embodiments, the elevating member is configured as a catheter hub and is fixedly connected to the proximal portion such as by way of overmolding.

In some embodiments, the elevating member is releasably or permanently connectable to a catheter hub fixedly connected to and/or molded over the proximal portion.

In some embodiments, the chosen angle is within a range of 20° to 90°, optionally about 45°.

In some embodiments, the chosen height is adjustable or fixed.

In some embodiments, vascular access line comprising two juxtaposing lumens, wherein the proximal portion includes a merging section, wherein the two juxtaposing lumens are divided between two distinct bodies extending proximally to the merging section, and divided by a wall in a unitary body extending distally to the merging section.

In some embodiments, the distal portion includes a first bent or curved section configured with a first radius of curvature and a first curve length when in an elastically relaxed state.

In some embodiments, the first bent or curved section is bent or curved upwards towards a plane coinciding with the bottom surface.

In some embodiments, the distal portion includes a second bent or curved section configured with a second radius of curvature and a second curve length when in an elastically relaxed state.

In some embodiments, the second bent or curved section is bent or curved downwards away from a plane coinciding with the bottom surface.

In certain embodiments there is provided a surgical tunneler, comprising a rigid elongated body, a rounded or pointed distal tip configured to dissect between tissue layers and/or to form a surgical tunnel when pushed subcutaneously in the body, and a guidewire capturing carabiner provided proximally adjacent to the distal tip. In some embodiments, the guidewire capturing carabiner is configured to capture or fasten to a target portion of a guidewire extending transversely thereto. In some embodiments, the guidewire capturing carabiner includes an elastically swingable gate shiftable laterally from a closed state towards a recess formed in the elongated body, when the gate is pressed against the target portion, and to elastically swing back to the closed state when the target portion extends through the recess and disengages from the gate.

In some embodiments, the surgical tunneler comprising a tissue cutting portion extending adjacent and/or parallel to the guidewire capturing carabiner, configured to cut through soft tissue between the guidewire capturing carabiner and the target portion.

In some embodiments, the tissue cutting portion includes a blade and/or cutting teeth.

In some embodiments, the tissue cutting portion extend along a length of the gate.

In some embodiments, the elongated body is shapeable to a fixed chosen contour.

In certain embodiments there is provided a kit, comprising the vascular access line and the surgical tunneler. In some embodiments, the kit further comprising a guidewire. In some embodiments, the kit further comprising an introducer, optionally comprising a splitable sheath placed over a dilator, configured to pass over the guidewire and to allow passing of the vascular access line therethrough.

In certain embodiments, there is provided a method for implanting an access line (e.g., a catheter or PICC line) in a body of a subject. The method/device can comprise:
  extending a guidewire along a preliminary insertion route within the body, between a first location on a skin of the subject and a bodily lumen, wherein a proximal end of the guidewire is outside the body and a distal end of the guidewire is inside the bodily lumen;
  folding into a loop a target portion of the guidewire inside the body;
  pulling the loop in the body to a second location on the skin, remote from the first location, wherein the guidewire follows a final insertion route within the body between the second location and the bodily lumen; and
  implanting the access line along the final insertion route.

In some embodiments, the method comprising advancing a guidewire manipulator from the second location towards the target portion, wherein the folding and/or the pulling is performed with the guidewire manipulator.

In some embodiments, the advancing forms a surgical tunnel from the second location to a target location in the body in proximity to the target portion of the guidewire.

The method according to claim 3, wherein the pulling includes passing the loop through the surgical tunnel towards the second location and/or out of the body through the second opening.

In some embodiments, the method comprising making an incision across the second location, wherein the advancing includes pushing the guidewire manipulator through the incision into the body.

In some embodiments, the guidewire manipulator is configured to facilitate selective hanging, fastening and/or locking to the guidewire.

In some embodiments, the guidewire manipulator includes a rounded distal tip configured to dissect between tissue layers and/or to form a surgical tunnel when pushed subcutaneously in the body.

In some embodiments, the guidewire manipulator includes an anvil portion and a pressing portion selectively movable one against the other, the method further includes pressing the guidewire between the pressing portion and the anvil portion to a chosen shape.

In some embodiments, the pressing causes a fixed deformation of the guidewire at or adjacent the target portion.

In some embodiments, the method comprising fixedly deforming the guidewire to form a local deviated portion at or adjacent to the target portion having reduced resistance to bending or folding relative to portions of the guidewire adjacent thereto.

In some embodiments, the guidewire includes a metal member or core being elastic or superelastic along the target portion, and the fixedly deforming includes plastically deforming the metal member or core.

In some embodiments, the folding includes or follows the fixedly deforming.

In some embodiments, when the guidewire is straightened, the local deviated portion has a maximal inclination smaller than 30° relative to long axis of the guidewire.

In some embodiments, the method comprising forming a surgical tunnel from the second opening to a target location in the body in proximity to the target portion.

In some embodiments, the pulling includes passing the loop through the surgical tunnel towards the second location.

In some embodiments, the target location is located between a cutis and a subcutis of the body, or within the subcutis, or distally adjacent to the subcutis.

In some embodiments, the pulling includes opening the loop and unrolling or straightening the guidewire, wherein the guidewire proximal end is outside the body and the guidewire distal end is inside the bodily lumen.

In some embodiments, the extending includes pushing a needle through the skin at the first location until penetrating the bodily lumen with a tip of the needle, passing the guidewire through the needle until the guidewire follows the preliminary insertion route, and removing the needle leaving the guidewire in-place.

In some embodiments, the implanting includes passing an introducer over the guidewire along the final insertion route, removing the guidewire from the body through the introducer, advancing an access line through the introducer along the final insertion route and in the blood vessel, and removing the introducer.

In some embodiments, the introducer is splitable along weakened seams provided therealong, and includes a dilator extending therethrough, wherein the removing the guidewire includes removing the dilator, and the removing the introducer includes splitting the introducer along the weakened seams.

In some embodiments, the final insertion route is substantially greater in length and/or inclined more gradually relatively to surface of the skin, than the preliminary insertion route, optionally particularly across a subcutis of the body.

In certain embodiments, there is provided a guidewire manipulator, comprising:
  a rigid elongated body; a rounded distal tip configured to dissect between tissue layers and/or to form a surgical tunnel when pushed subcutaneously in the body; and a guidewire capturing portion adjacent to the distal tip, configured to capture or fasten to a target portion of a guidewire, such that the guidewire can be folded and/or withdrawn from the target portion when drawn by the guidewire manipulator when the guidewire capturing portion engages the target portion.

In some embodiments, the guidewire manipulator comprising a guidewire deforming mechanism configured to fixedly deform the guidewire, selectively, when the guidewire capturing portion engages the target location, sufficiently to form a local deviated portion, at or adjacent to the target portion, having reduces resistance to bending or folding relative to portions of the guidewire adjacent thereto.

In some embodiments, the guidewire capturing portion is hook shaped.

In some embodiments, the elongated body is shapeable to a fixed chosen contour.

In some embodiments, the guidewire deforming mechanism includes an anvil portion and a pressing portion selectively movable one against the other and configured to press the guidewire therebetween to a chosen shape for forming the local deviated portion.

In some embodiments, the chosen shape includes a U-shape comprising a bend radius being at least 3 times a radius of the target portion.

In some embodiments, the guidewire deforming mechanism includes a tubular member selectively slidable axially over the elongated body, wherein the tubular member includes the pressing portion.

In some embodiments, the elongated body includes the anvil portion.

In some embodiments, the tubular member and/or the pressing portion includes a deformable portion configured to conform at least partially to and over the chosen shape imposed by the guidewire when pressed by the pressing portion against the anvil portion.

In some embodiments, the deformable portion is configured to fixedly deform in accordance with the chosen shape when pressing the guidewire against the anvil portion.

In certain embodiments, there is provided a kit comprising a guidewire and the guidewire manipulator.

In some embodiments, the kit further comprising an access line, optionally comprising a catheter.

In some embodiments, the kit further comprising an introducer, optionally comprising a splitable sheath placed over a dilator, configured to pass over the guidewire and to allow passing of the access line therethrough.

All technical or/and scientific words, terms, or/and phrases, used herein have the same or similar meaning as commonly understood by one of ordinary skill in the art to which the invention pertains, unless otherwise specifically defined or stated herein. Illustrative embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE DRAWINGS

Some embodiments are herein described, by way of example only, with reference to the accompanying drawings. With specific reference now to the drawings in detail, it is stressed that the particulars shown are by way of example and for purposes of illustrative description of some embodiments. In this regard, the description taken together with the accompanying drawings make apparent to those skilled in the art how some embodiments may be practiced.

In the drawings:

FIGS. 3A-3B illustrate views of an exemplary vascular access line, according to some embodiments;

DETAILED DESCRIPTION

Figure 1A:
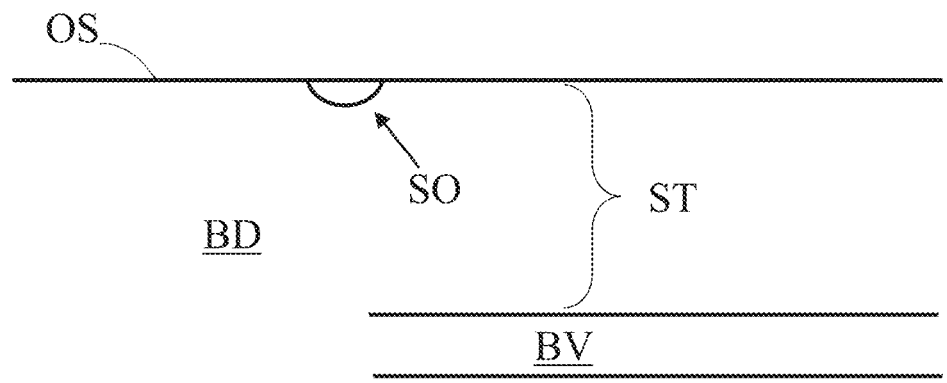
FIG. 1A schematically illustrates a cross sectional view of a portion of a body of a subject showing an exemplary portion of a blood vessel.

Certain embodiments relate to devices and methods for implanting access lines such as catheters, and more particularly, but not exclusively, to kits, devices and methods for implanting access lines through surgical tunnels.

Veins in the body are larger as they are more central. Nowadays, vascular access lines such as PICC lines are placed in the basilic, brachial or the cephalic vein. Current implantation site and entry into the body and the vasculature is in the mid to lower arm, to allow easy access to the catheter. However, a more centrally located vein, for instance in the axillary vein, can be advantageous since it is much larger in diameter and thus less prone to thrombosis due to the high blood flow rate applicable for access lines. Using currently known devices and methods for implanting PICC lines in central veins is found less preferred because such vessels are not easily accessible and can be more prone to infections. For placing vascular access lines, thought should also be given to the shape and magnitude of mechanical stress applied to the hosting blood vessel, particularly in proximity to the catheter entrance into the blood vessel.

Disclosed herein, are devices, kits and methods for placing a tunneled line which can allow placement of a vascular access line such as a catheter (e.g., PICC line) along a surgically formed subcutaneous tunnel, therefore enabling access to a larger, more central vein (while appearing as a regular PICC) for infusing medication and/or drawing blood even on a daily basis. The access into the vessel can be more central and the exit site from the skin can be similar or substantially identical, and appearing as a regular non-tunneled PICC. Such methods and devices may also serve to increase the length of the subcutaneous tunnel and the distance between the skin incision and the vascular system, making the distance that the bacteria need to pass to reach the bloodstream much longer, thus reducing the risk of infections and/or thrombosis.

In some embodiments, a vascular access line is configured to prevent or reduce accumulation of dirt and bacteria on the skin, and/or to allow easy cleaning thereof, in proximity to the surgical opening made in the skin through which the vascular access line enters the body of the subject. Alternatively or additionally, the vascular access line in some embodiments is configured to reduce mechanical stress of the hosting blood vessel in proximity to the catheter insertion area therein via the covering skin layers or via a surgical tunnel made across the skin layers to the blood vessel.

In some embodiments, a guidewire is first inserted from a first location on a skin of a subject (e.g., human patient) along a preliminary insertion route into a bodily lumen (e.g., a blood vessel or a cavity in an organ), then rerouted to follow a final insertion route to same bodily lumen from a second location on the skin. In some such embodiments, the guidewire is rerouted from inside the body such that a distal part of the guidewire substantially maintains its route and a proximal part of the guidewire is rerouted. Optionally, the proximal part of the guidewire is rerouted to follow a length slightly inclined to skin surface, across the underlying subcutaneous layers, then exits the body via the second location. In some embodiments, the rerouted proximal guidewire part follows a route being greater in length and inclined more gradually (i.e., less steep) relatively to skin surface, than the original (preliminary) route across the subcutaneous layers.

In some embodiments, a surgical tunneler is used to first form a surgical tunnel from a surgical opening to the body of the subject to a target location adjacent to a portion of a guidewire emerging from a target blood vessel, and then to capture the guidewire portion and pull it back through the surgical tunnel and out of the body via the surgical opening. The surgical tunneler or a dedicated guidewire manipulator, may be configured and used for first accessing and engaging the portion of the guidewire inside the body, then for manipulating the guidewire at or in proximity to the target portion, such as by folding the target portion into a loop, and then for pulling the guidewire at the loop along the final insertion route and out through the second location on the skin. The first location and/or the preliminary insertion route may be advantageous for initially accessing the bodily lumen with the guidewire, while the second location and/or the final insertion route may be advantageous for implanting an access line or a catheter over the guidewire, particularly if it is intended for prolonged implantation such as for days, weeks, months or more. The target blood vessel may be the internal jugular vein with access thereto located below the clavicle. Alternatively, the target blood vessel may be one or more of the basilic vein, the brachial vein, the axillary vein, and the femoral veins. An important advantage of using this method of rerouting the guidewire via a surgical tunnel across the subcutaneous, from within the body, is the formation of a single incision only, at the second location, which is found preferred for preventing or reducing risk of infection and scarring. Since that initial access via the first location is done with a small diameter needle, it usually leaves only a small mark which is naturally healed within hours to a few days without leaving permanent marking or causing infection.

Figure 1B:
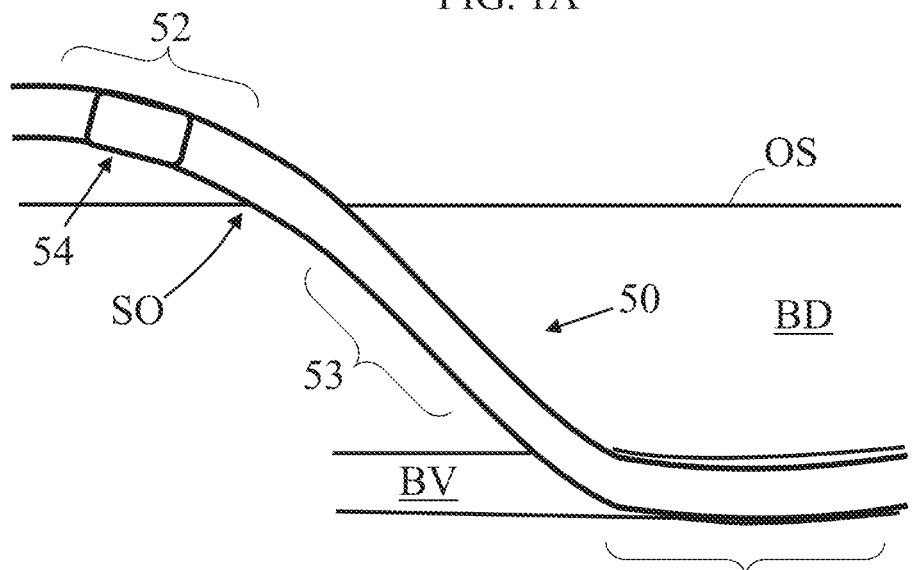
FIGS. 1B-1C schematically illustrate cross sectional views of a prior art vascular access line at two separate scenarios when introduced into the blood vessel in the body illustrated in FIG. 1A.
Figure 1C:
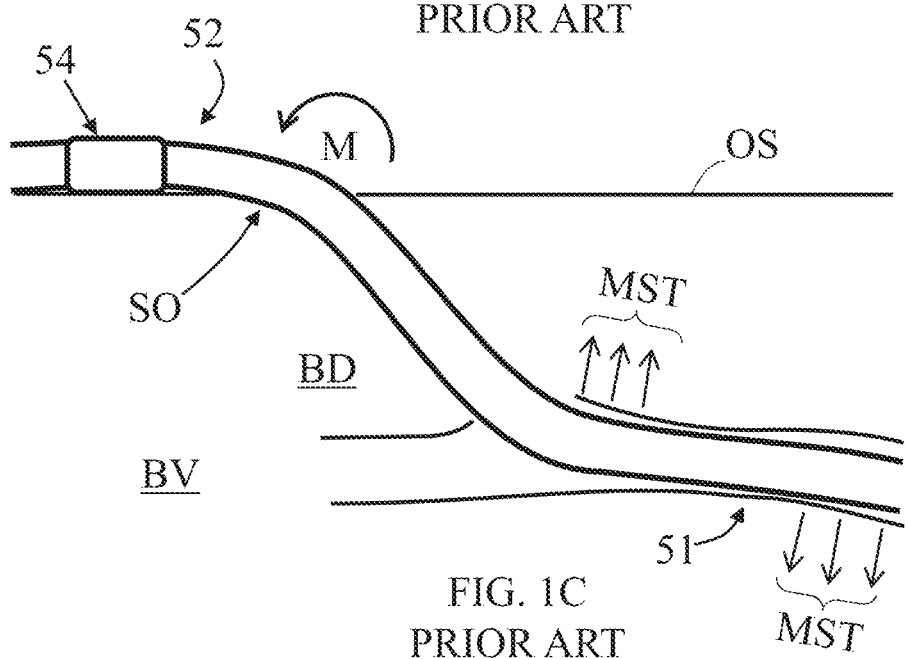

FIG. 1A schematically illustrates a cross sectional view of a portion of body BD showing a skin outer surface OS of body BD, underlying subcutaneous tissues ST, and a portion of a blood vessel BV (e.g., Axillary vein, Basilic vein, Brachial vein, or Cephalic vein) beneath subcutaneous tissues TS. FIGS. 1B-1C schematically illustrate cross sectional views of a prior art vascular access line 50 at two separate scenarios when introduced into blood vessel BV. As shown in the first instance illustrated in FIG. 1B, a distal portion 51 of access line 50 is positioned in blood vessel BV, a proximal portion 52 of access line 50 emerges from a surgical opening SO outside of body BD in a relatively loose form, and an intermediate portion 53 of access line 50, extending between proximal portion 52 and distal portion 51, passes at an angle through skin layers forming subcutaneous tissues ST. A hub 54 is connected (e.g., molded) over proximal portion 52. Hub 54 is fixedly attachable to body BD such as by way of adhesion or suturing to skin outer surface OS, although in the first instance it is unattached thereto.

Figure 2A:
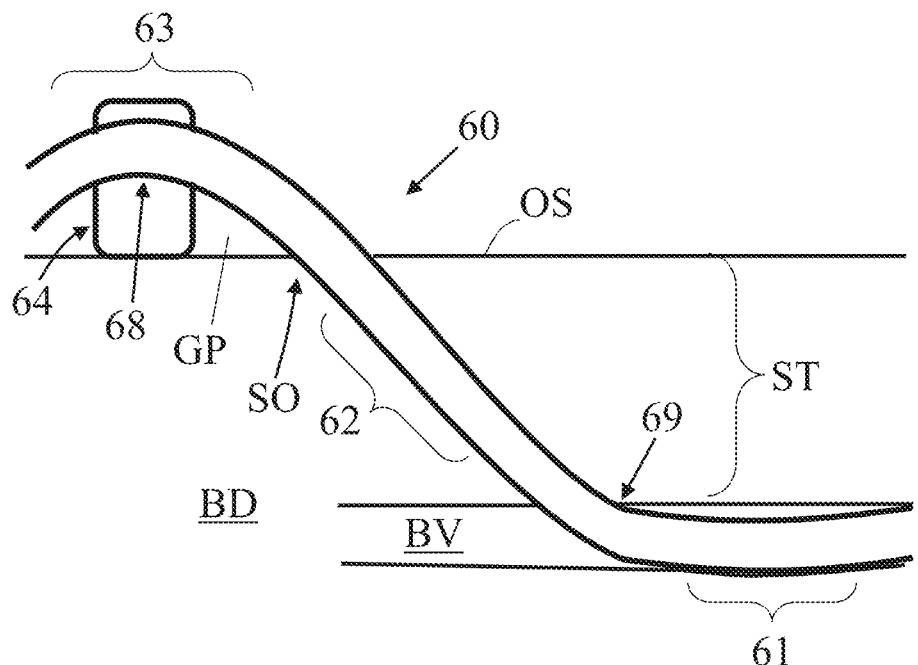
FIG. 2A schematically illustrates a cross sectional view of an exemplary vascular access line introduced into the blood vessel in the body illustrated in FIG. 1A, according to some embodiments.
Figure 2B:
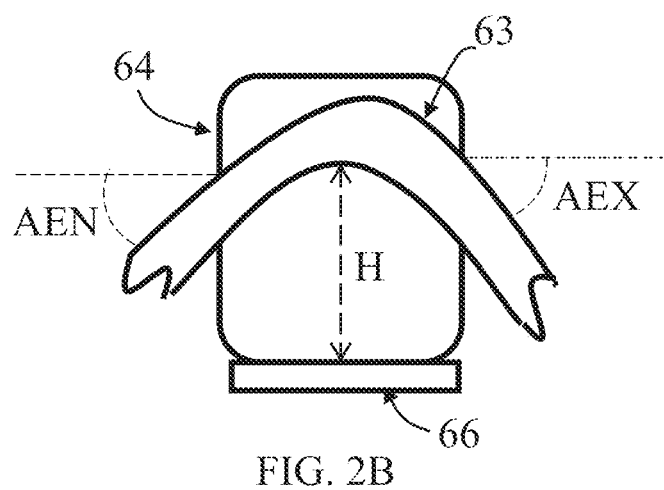
FIG. 2B schematically illustrates an enlarged cross-sectional view of a proximal portion of the exemplary vascular access line shown in FIG. 2A, according to some embodiments.
Figure 2C:
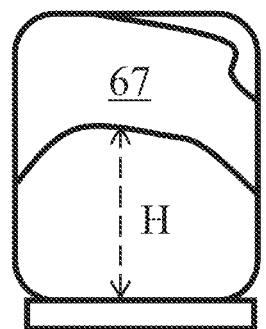
FIGS. 2C-2D schematically illustrate cross sectional views of an exemplary elevating member before and after deployment of an exemplary vascular access line therein, respectively, according to some embodiments.

In the second instance shown in FIG. 2C hub 54 is attached to skin outer surface OS in proximity (usually up to a few centimeters). Since that access line 50 is normally straight and has significant rigidity (similarly to commonly available prior art PICC lines, for example), lowering of proximal portion 52 towards outer surface OS, as would normally be a required precondition for attaching hub 54, generates a moment M which causes mechanical stresses MST in blood vessel BV in contact with distal portion 51. Since that blood vessel BD is held in a deformed state caused by mechanical stresses MST for prolonged period, this may cause and/or result in permanent damage to blood vessel BV and subsequent illness. Furthermore, attaching hub 54 also results in attaching body of access line 50 to skin outer surface OS adjacent to surgical opening SO, such that it does not provide a minimal gap necessary for adequately cleaning around the surgical opening. This way, dirt and bacteria can be accumulated adjacent to surgical opening SO and can cause infection.

FIG. 2A schematically illustrates a cross sectional view of a vascular access line 60 introduced into blood vessel BV and deployed, which is configured to address one or more of the issues discussed with respect to prior art access line 50. Access line 60 includes a distal portion 61 configured for placement in blood vessel BV, an intermediate portion 62 configured to pass through surgical opening SO and extend across skin layers ST in body BD, and a proximal portion 63 configured to reside outside body BD. Access line 60 has one or more bent or curved segment, when in an elastically relaxed state, that are optionally formed at manufacturing stage, in order that mechanical moments and/or stresses affecting surrounding bodily tissues will be prevented or reduced. In some embodiments, access line 60 has a first bent or curved segment 68 along proximal portion 63 and/or between proximal portion 63 and intermediate portion 62 in order to diminish or prevent formation of moment M adjacent to surgical opening SO. In some embodiments, access line 60 has a second bent or curved segment 69 along distal portion 61 and/or between distal portion 61 and intermediate portion 62 in order to prevent significant reshaping or causing mechanical stress MST to blood vessel BV.

Access line 60 further includes an elevating member 64 fixedly attachable to body BD at skin outer surface OS. Elevating member 64 is configured to route proximal portion 63 at a chosen height H, a chosen route shape and orientation, a chosen angle of entry AEN (from proximal side of elevating member 64) and/or a chosen angle of exit AEX (from distal side of elevating member 64), as shown in FIG. 2B; such that one or more of these parameters is user-adjustable or predetermined. As such, elevating member 64 is configured to assist in preventing or reducing moment M since that no bending of access line 60 is needed for attaching it to body BD. Furthermore, height H of proximal portion 63 and its orientation are configured to form a gap GP adjacent to surgical opening SO after deployment and attachment of access line 60 to body BD, which is sufficiently large to allow cleaning and disinfection of this area.

Figure 2D:
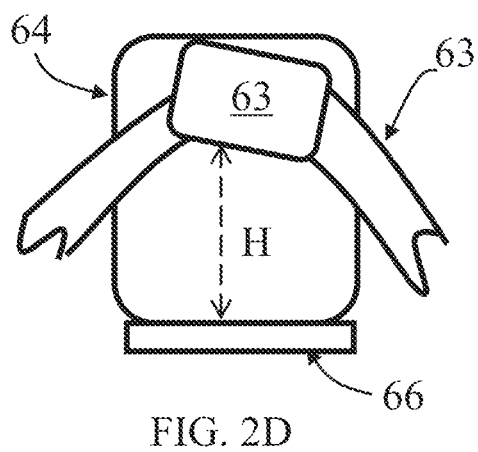

FIG. 2B schematically illustrates an enlarged cross-sectional view of proximal portion 63 in a first exemplary embodiment, wherein elevating member 64 is configured as a catheter hub and is fixedly connected to proximal portion 63, such as by way of overmolding. FIGS. 2C-2D schematically illustrate cross sectional views of another example for elevating member 64 before and after deployment of an exemplary vascular access line therein, respectively, wherein elevating member 64 is releasably or permanently connectable to a catheter hub 65 which is fixedly connected to and/or molded over proximal portion 63. Elevating member 64 comprising a bottom surface 66 and is fixedly attachable to body BD at skin outer surface OS. Elevating member 64 includes an elevated channel 67 provided at a chosen height relative to bottom surface 65. Elevating member 64 is configured to accommodate (in the second example) and/or hold proximal portion 63 within elevated channel 67 in a chosen shaped route (optionally imposed by elevated channel 67) above bottom surface 66, when elevating member 64 is attached to body BD, such that intermediate portion 62 is fixed at a chosen angle AEX relative to bottom surface 66 and/or to blood vessel BV, when intermediate portion 62 is in an elastically relaxed state.

FIGS. 3A-3B illustrate views of an exemplary vascular access line 100, which may be similar or identical in at least one structural and/or functional embodiment to access line 60, or it may be an exemplary configuration or exemplary variation of access line 60. Access line 100 is optionally a multi-lumen catheter (e.g., double-lumen catheter having two juxtaposing lumens), such as a hemodialysis catheter or a Periphery Inserted Central Catheter (also known as 'PICC line'). Vascular access line 100 includes a distal portion 101 configured for placement in a blood vessel in a body of a subject, an intermediate portion 102 configured to pass through a surgical opening and extend across skin layers in the body, and a proximal portion 103 configured to reside outside the body. Proximal portion 103 includes a merging section 110, wherein the two juxtaposing lumens are divided between two distinct bodies extending proximally to merging section 110, and divided by a wall in a unitary body extending distally to merging section 110.

Access line 100 further includes an elevating member 104 comprising a bottom surface 105 and an elevated channel (similar to elevated channel 67) provided at a chosen height (e.g., adjustable or fixed height) relative to bottom surface 105. Elevating member 104 is configured as a catheter hub and is fixedly connected to proximal portion 103 and/or merging section 110, such as by way of overmolding. Elevating member 104 is attachable to the body, such as by way of adhesion (e.g., using catheter securing adhesive and/or dressing) and/or suturing (via eyelets 107) to an outer skin surface of the body.

Elevating member 104 is configured to accommodate and/or hold proximal portion 103 within the elevated channel in a curved shaped route above bottom surface 105, when elevating member 104 is fixedly attached to the body. The curved shaped route has an apex 108 pointing away from (upwards) bottom surface 105. As such, intermediate portion 102 is fixed at a chosen angle 109 relative to bottom surface 105 and/or the blood vessel, when access line 100 (or at least intermediate portion 102) is in an elastically relaxed state. Chosen angle 109 is within a range of about 20° to about 90°, optionally particularly within a range of about 30° to 60° (e.g., about 45°).

Distal portion 101, when in an elastically relaxed state, includes a first bent or curved section 111 configured with a first radius of curvature and a first curve length, and a second bent or curved section 114 configured with a second radius of curvature and a second curve length. First bent or curved section 111 is curved upwards towards a plane coinciding with bottom surface 105, and second bent or curved section 114 is curved downwards away from the same plane coinciding with bottom surface 105. The distance between first bent or curved section 111 and intermediate portion 102 is optionally within a range of 3 mm to 50 mm, first radius of curvature is optionally within a range of 5 mm to 50 mm, and first curved length is optionally within a range of 5 mm to 50 mm. The distance between second bent or curved section 114 and first bent or curved section 111 is optionally within a range of 0.5 mm to 30 mm, second radius of curvature is optionally within a range of 5 mm to 50 mm, and/or second curved length is optionally within a range of 0.5 mm to 40 mm.

Figure 4A:
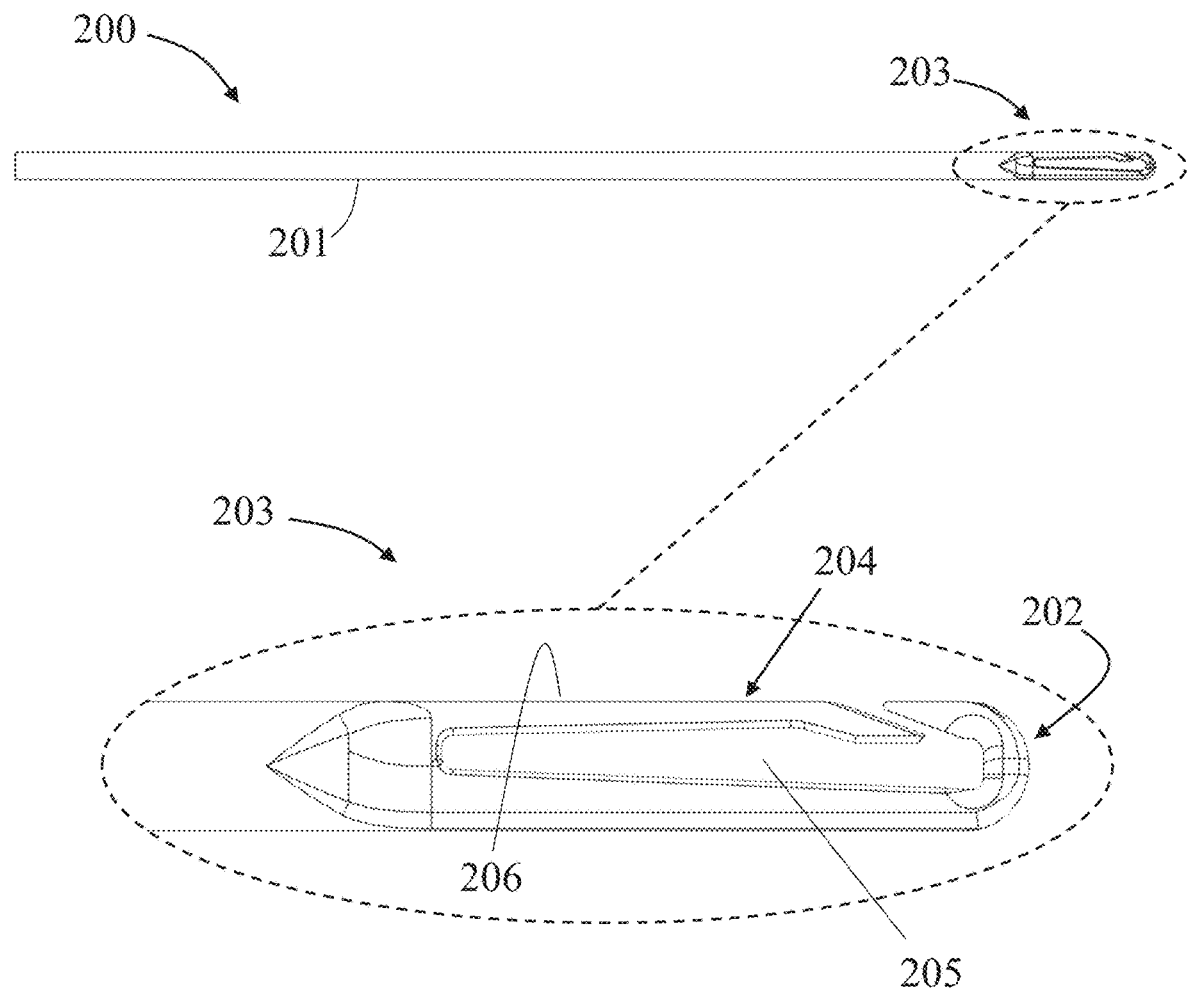
FIGS. 4A-4B illustrate views of an exemplary surgical tunneler, according to some embodiments.
Figure 4B:
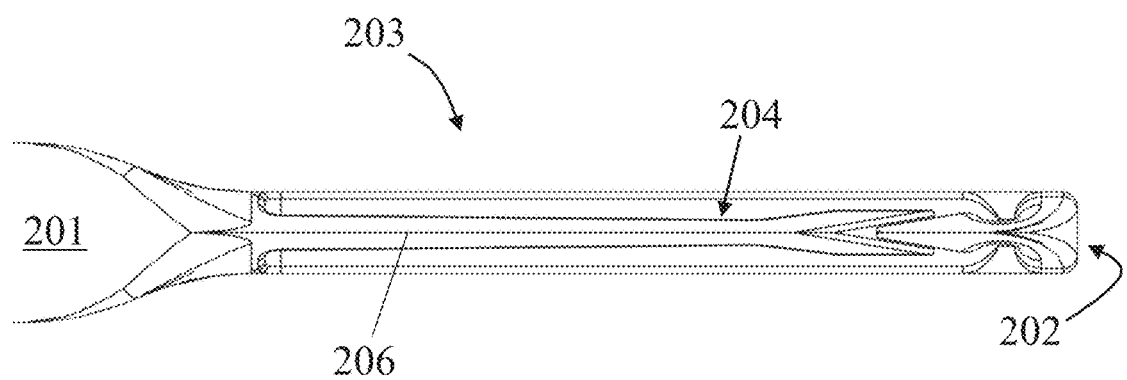

FIGS. 4A-4B illustrate views of an exemplary surgical tunneler 200, configured to form a surgical passage between subcutaneous tissue layers when pushed therebetween with sufficient manual force. Surgical tunneler 200 includes a rigid elongated body 201 and a rounded or pointed distal tip 202, configured to dissect between tissue layers and/or to form a surgical tunnel when pushed subcutaneously in the body. Elongated body 201 is optionally substantially straight in form and sufficiently rigid to maintain its original form when in use for forming a surgical tunnel, or alternatively it may be shapeable to a fixed chosen contour.

Surgical tunneler 200 further includes a guidewire capturing portion configured as a carabiner 203, which is provided proximally adjacent to distal tip 202. Guidewire capturing carabiner 203 is configured to capture and/or fasten to a target portion of a guidewire extending transversely thereto. Guidewire capturing carabiner 203 includes an elastically swingable gate 204 shiftable laterally from a closed state (as shown in the enlarged view of FIG. 4A, for example) towards a recess 205 formed in elongated body 201, when gate 204 is pressed against the guidewire target portion. When the guidewire target portion extends through recess 205 and disengages from gate 204, the gate 204 can elastically swing back to the closed state and lock the guidewire in the recess 205. Once locked, the target portion of the guidewire can be pulled back through the surgical tunnel initially formed by surgical tunneler 200 via a surgical opening (e.g., surgical opening SO) so that the guidewire can be rerouted and will emerge out of subject's body via the surgical opening formed into the surgical tunnel (passage) instead of via an initial entry point through which the guidewire was initially inserted.

Surgical tunneler 200 includes a tissue cutting portion 206 extending adjacent and in parallel to guidewire capturing carabiner 203 (optionally extend along a length of gate 204, as shown), and is configured to cut through soft tissue between guidewire capturing carabiner 203 and the guidewire target portion if such is entrapped therebetween after forming the surgical tunnel. Tissue cutting portion 206 may include a blade (as shown), cutting teeth and/or other tissue cutting or resecting means.

Figure 5A:
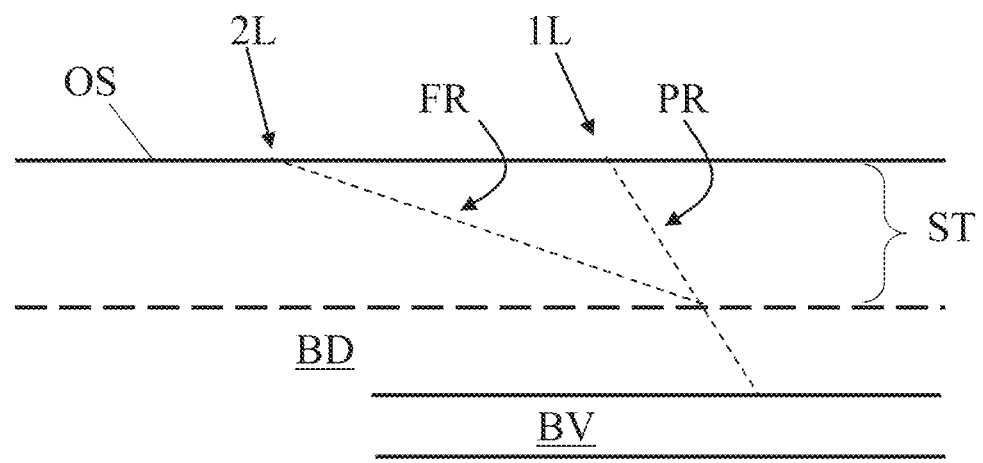
FIGS. 5A-5N schematically illustrate exemplary scenarios representing steps in an exemplary method for implanting an access line in a body of a subject, according to some embodiments.
Figure 5B:
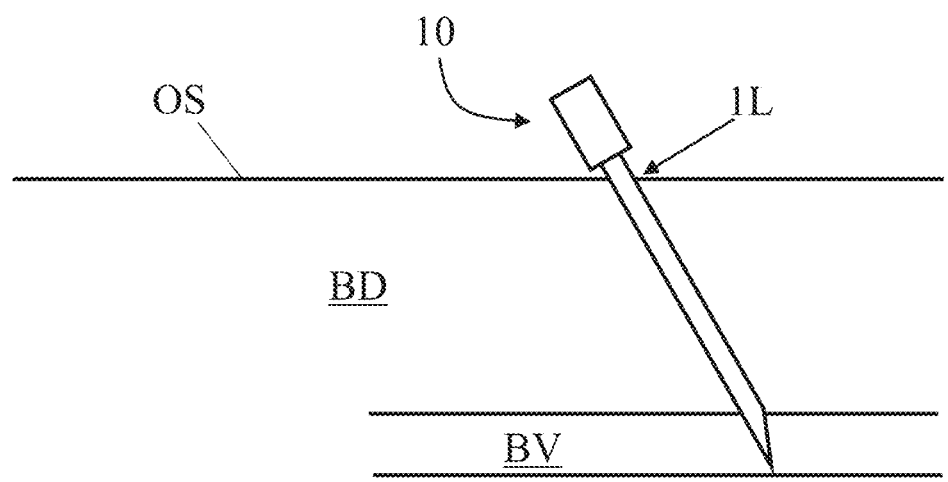
Figure 5C:
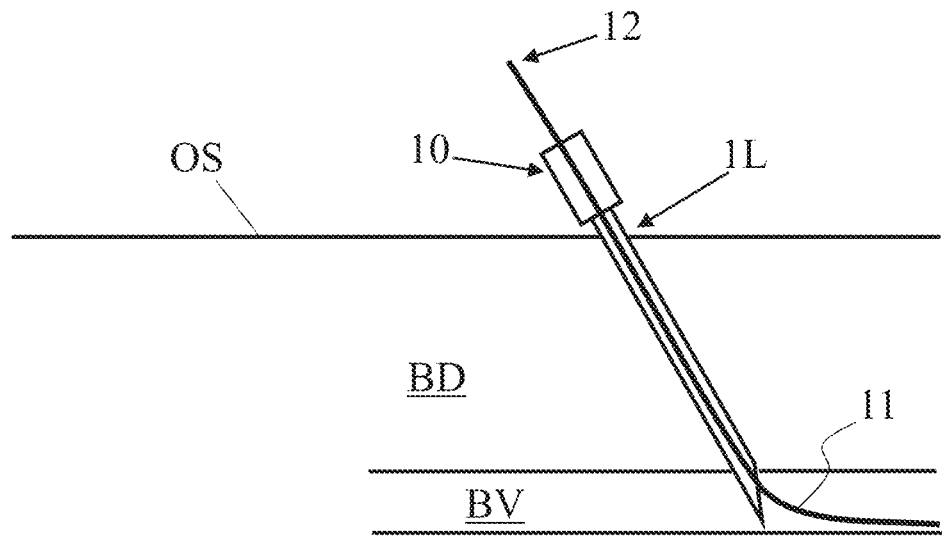
Figure 5D:
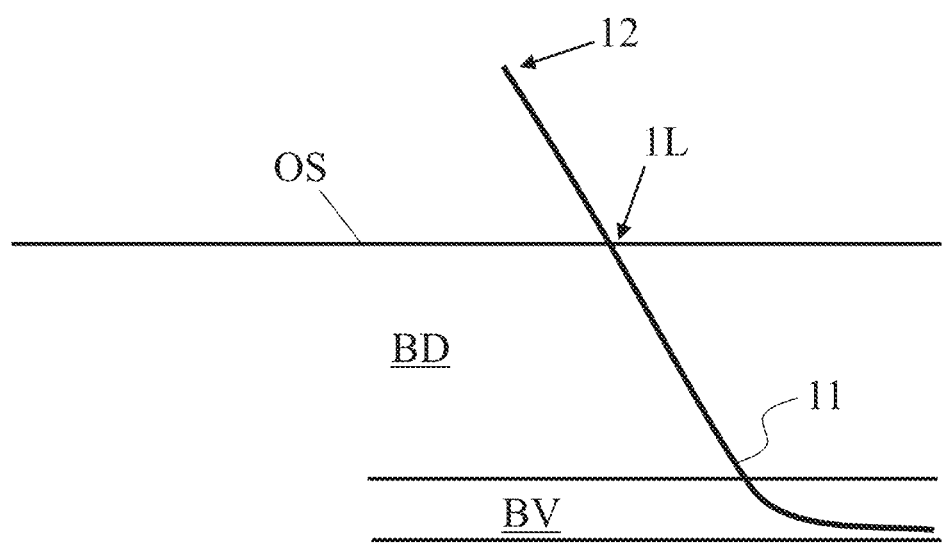
Figure 5E:
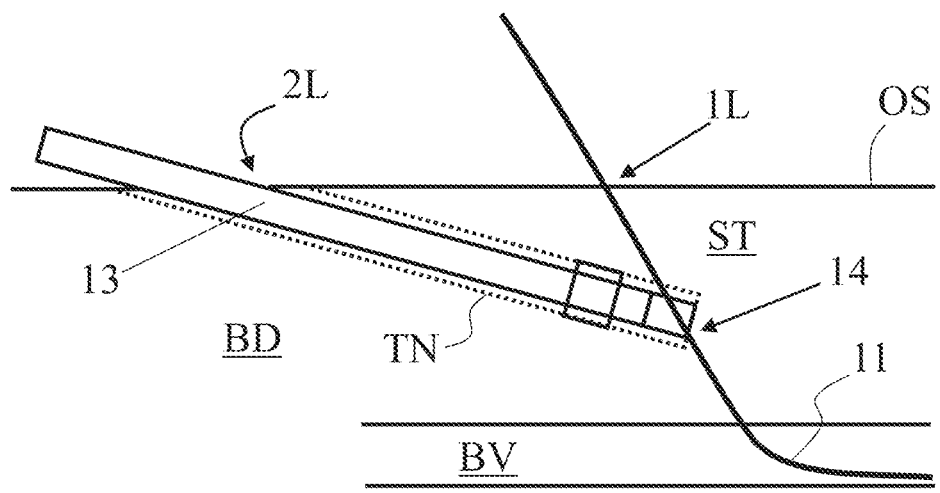
Figure 5F:
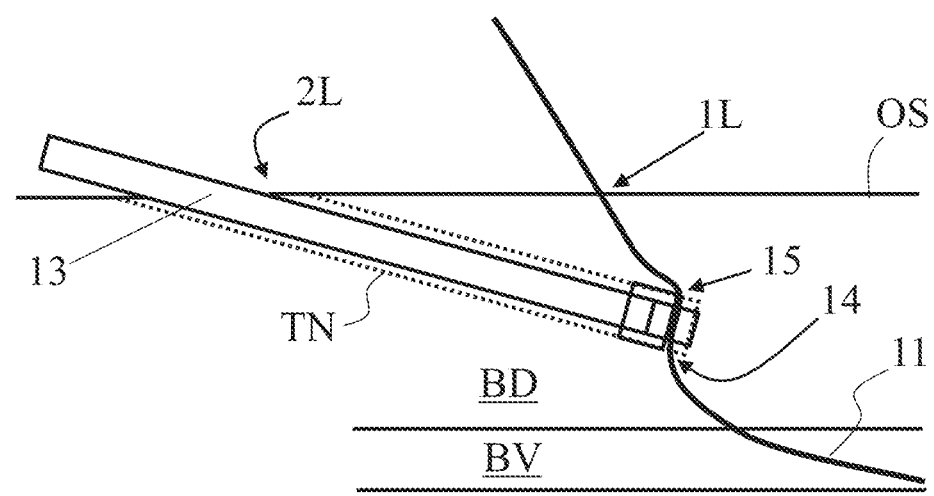
Figure 5G:
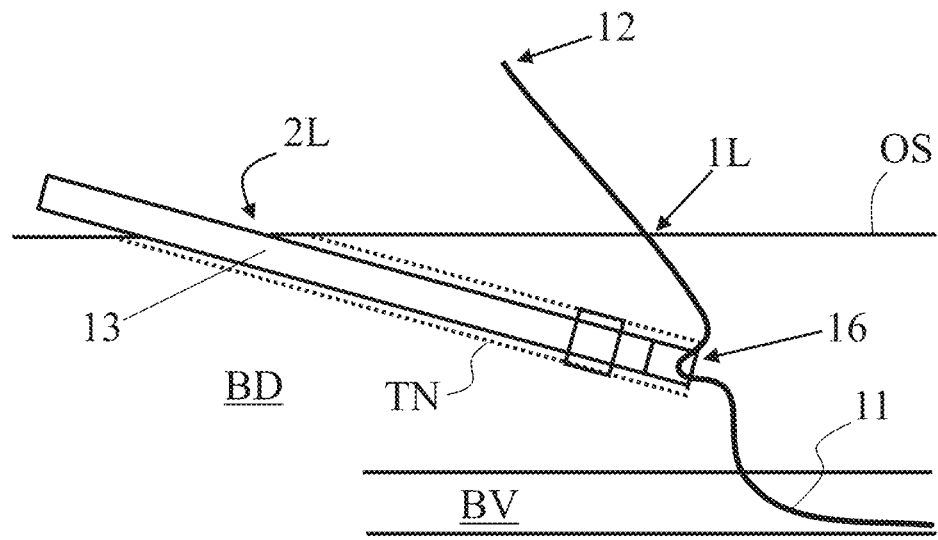
Figure 5H:
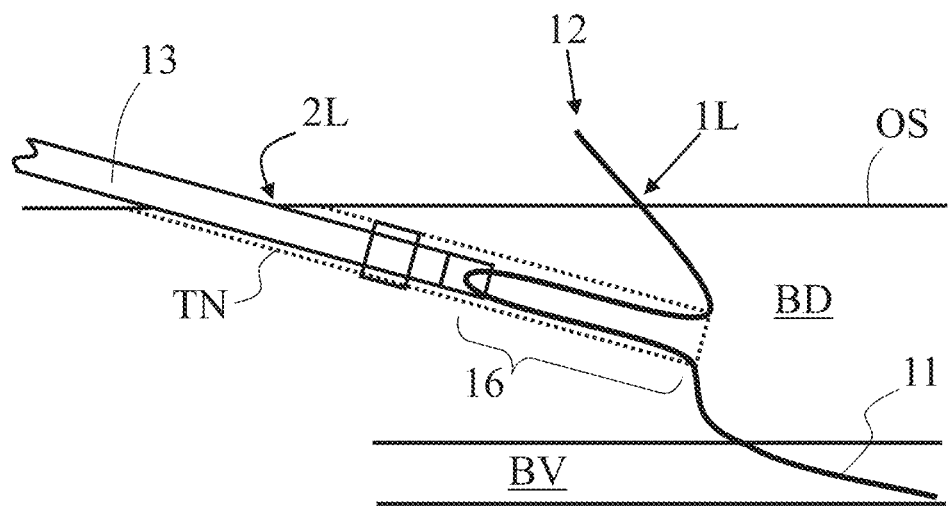
Figure 5I:
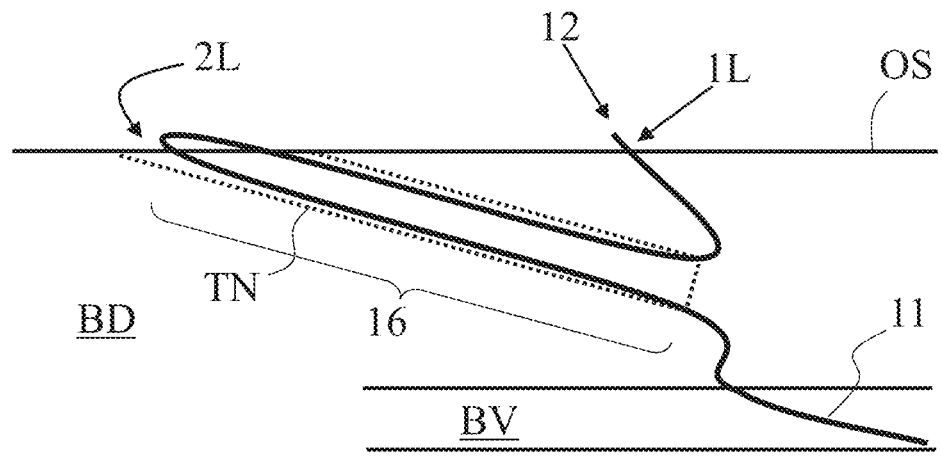
Figure 5J:
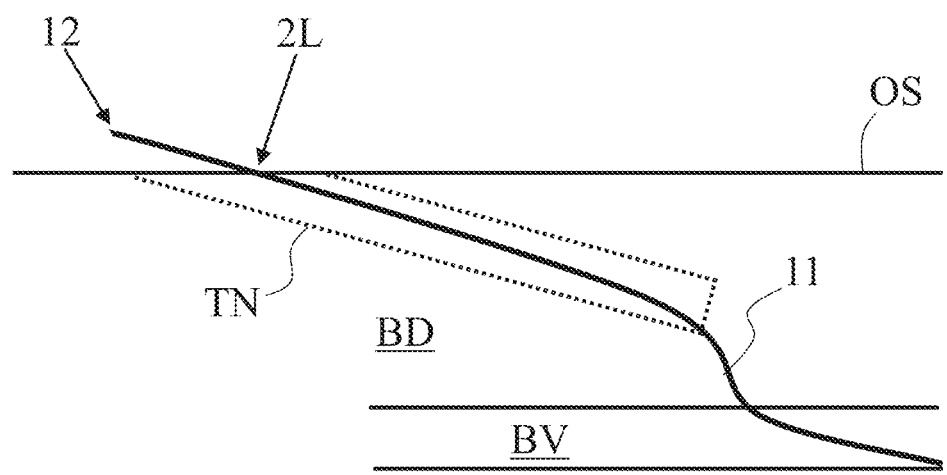
Figure 5K:
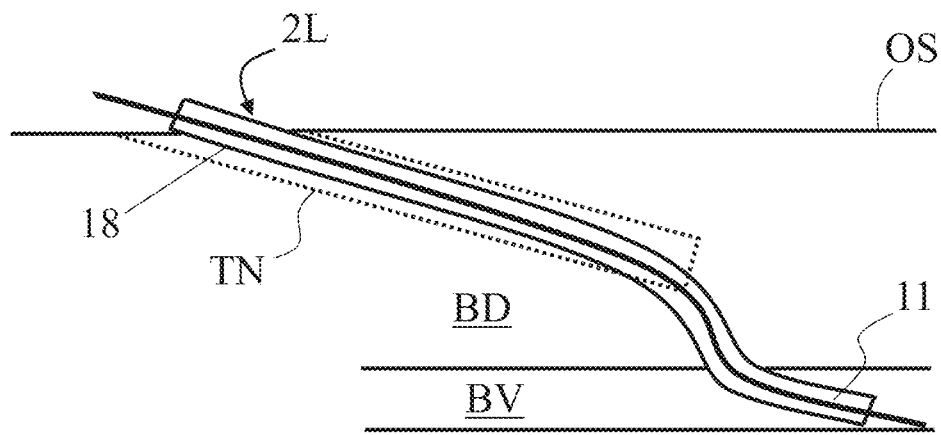
Figure 5L:
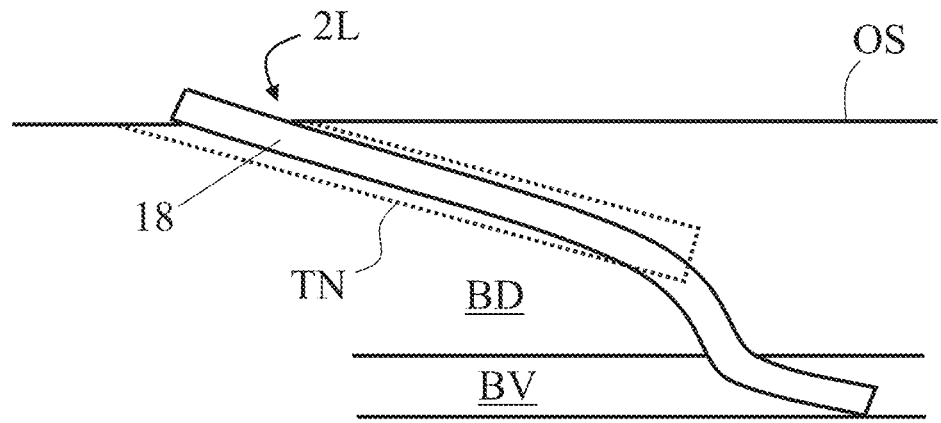
Figure 5M:
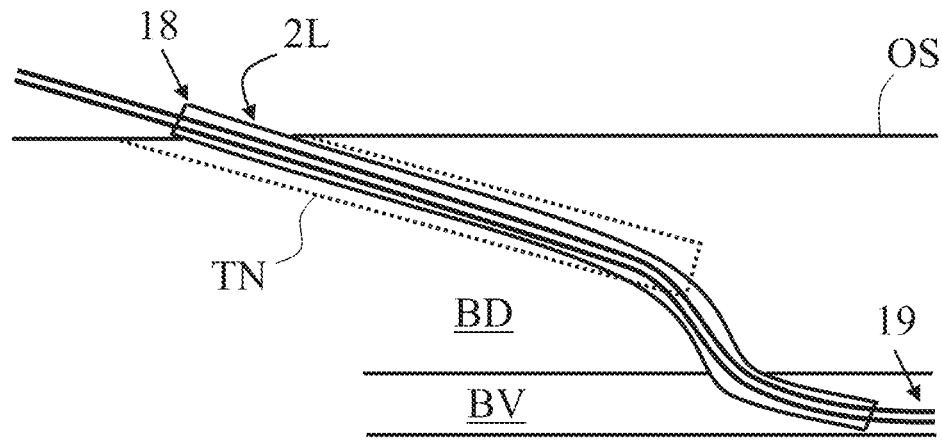
Figure 5N:
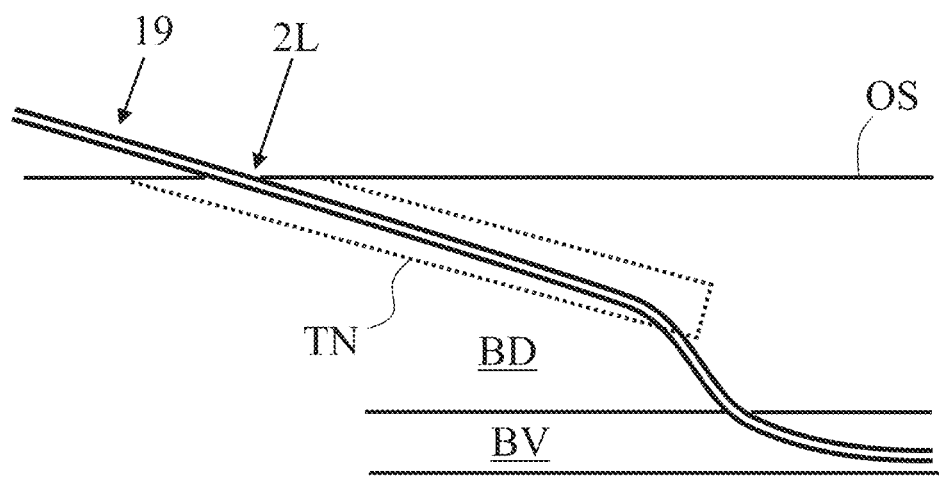

FIGS. 5A-5N schematically illustrate exemplary scenarios representing steps in an exemplary method for implanting an access line in a body BD of a subject SB. FIG. 5A illustrates a cross sectional view of a portion of body BD showing a skin outer surface OS of body BD, underlying subcutaneous tissues ST, and shortly beneath it a bodily lumen in a form of a blood vessel BV. At a preliminary stage, the medical practitioner can determine or choose one or more of a first location 5L, a preliminary insertion route PR, a second location 2L and a final insertion route FR. In some embodiments, final insertion route FR is substantially greater in length and inclined more gradually (i.e., less steep) relatively to skin surface, than preliminary insertion route PR, optionally particularly across subcutaneous tissues ST, as shown. FIG. 5B illustrates an exemplary access needle 10 after it has penetrated through first location 5L, across skin tissues, and into blood vessel BV with distal tip thereof, thereby forming preliminary insertion route PR for guidewire insertion. As shown in FIG. 5C, a guidewire 11 is advanced distally through access needle 10 until its distal end is in a chosen position inside blood vessel BV or in an organ cavity (e.g., a heart chamber) opened to blood vessel BV, and a proximal end 12 thereof is outside body BD. After a chosen positioning of guidewire 11 is met, access needle 10 is removed, leaving guidewire 11 extending along the preliminary insertion route PR (FIG. 5D).

For forming final insertion route FR, an incision is made on skin outer surface OS at (over or across, for example) second location 2L and a guidewire manipulator 13, configured as a surgical tunneler, is advanced therethrough towards a target portion 14 of guidewire 11 inside body BD, as shown in FIG. 5E. Target location 14 is optionally located between the cutis (skin dermis and epidermis) and subcutis (i.e., subcutaneous tissue ST) of body BD, or within the subcutis, or distally adjacent to the subcutis. Guidewire manipulator 13 includes a rounded distal tip configured to dissect between tissue layers, and is forcefully pushed through the subcutaneous tissues ST underlying skin outer surface OS thereby forming a surgical tunnel TN by advancing, from second location 2L to a target location in body BD in proximity to target portion 14 of guidewire 11.

Guidewire manipulator 13 is configured to facilitate selective hanging, hooking, fastening and/or locking to guidewire 11, such as at target portion 14 thereof, as shown in FIG. 5E. Furthermore, once connected or hooked to guidewire 11, guidewire manipulator 13 can be selectively applied to manipulate a portion of guidewire 11 to fixedly (plastically) deform it. As shown in FIG. 5F, guidewire 11 can be fixedly deformed by guidewire manipulator 13 to form a local deviated portion 15 at or adjacent to target portion 14, which has reduced resistance to bending or folding relative to portions of the guidewire adjacent thereto, so that the next steps which involves folding to loop and pulling the loop can be facilitated or at least eased substantially. In some embodiments, local fixed deformation of a portion of guidewire 11 may be applied such as if the guidewire includes a metal core and/or if it is assessed or determined that surrounding tissues could be harmed when the guidewire is pulled laterally from within the body, as described hereinafter.

Following forming of deviated portion 15, guidewire 11 is pulled by guidewire manipulator 13 at target portion 14, deviated portion 15, or in between them, thereby folding target portion 14 into a loop 16 (FIG. 5G). Guidewire 11 is further pulled by guidewire manipulator 13 which is withdrawn in surgical tunnel TN towards second location 2L and gradually pulls and enlarges loop 16 (FIG. 5H) until it is completely withdrawn and removed from body BD with loop 16 located in proximity to second location 2L and optionally emerges proximally therethrough (FIG. 5I). Guidewire 11 can then be unrolled and/or straighten, and loop 16 can be opened, such as by pulling guidewire's proximal part while leaving its distal part in place, until it follows the final insertion route FR, as shown in FIG. 5J, with its proximal end 12 extending outside the body BD via second location 2L and its distal end positioned in the chosen bodily lumen (e.g., in blood vessel BV or in an organ cavity opened thereto). In some embodiments, guidewire 11 is pulled by guidewire manipulator 13 from a specific target portion of guidewire 13. In some such embodiments, guidewire manipulator 13 is fastened onto the target portion of guidewire 13 throughout most or all pulling or withdrawal of guidewire 11 through surgical tunnel TN towards second location 2L. In some other embodiments, guidewire manipulator 13 is not fastened to, or is sequentially fastened to and released from, guidewire 11, so that different portions of guidewire 11 are pulled by guidewire manipulator 13 when guidewire 11 is withdrawn through surgical tunnel TN towards second location 2L.

The now (fully or partially) straighten or unrolled guidewire 11 extending along the final insertion route FR can be used for delivering a catheter introducer 18. Introducer 18 shown in FIG. 5K includes a lumen with which it can be placed over and advanced over guidewire 11 until fully extending along final insertion route across the incision at second location 2L and reaching into the bodily lumen (e.g., blood vessel BV) with distal end thereof. Once introducer 18 is properly positioned, guidewire 11 can be pulled and removed from body BD through the introducer (FIG. 5L). Introducer 18 may include a dilator extending therethrough, so removing of guidewire 11 may follow or include removing of dilator from introducer 18. Once introducer 18 is patent, an access line or catheter 19 can be advanced through introducer 18 along final insertion route FR and in the blood vessel BV (FIG. 5M), and then the introducer 18 can be removed leaving access line or catheter 19 implanted in body BD (FIG. 5N). Optionally, introducer 18 is splitable along weakened seams provided therealong, so its removal from body BD involves its splitting along the weakened seams.

Figure 6A:
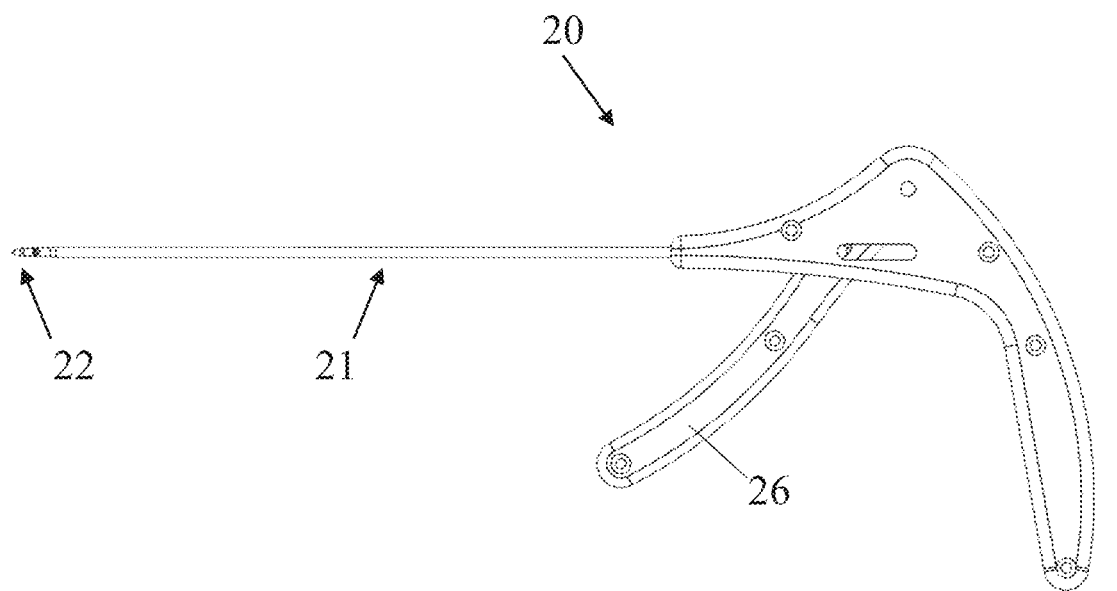
FIGS. 6A-6D illustrate views of an exemplary guidewire manipulator, according to some embodiments.
Figure 6B:
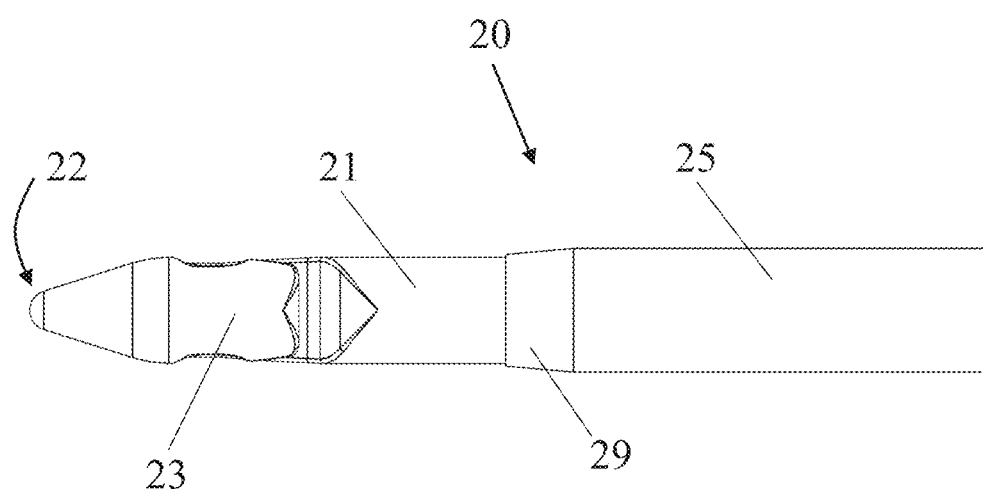
Figure 6C:
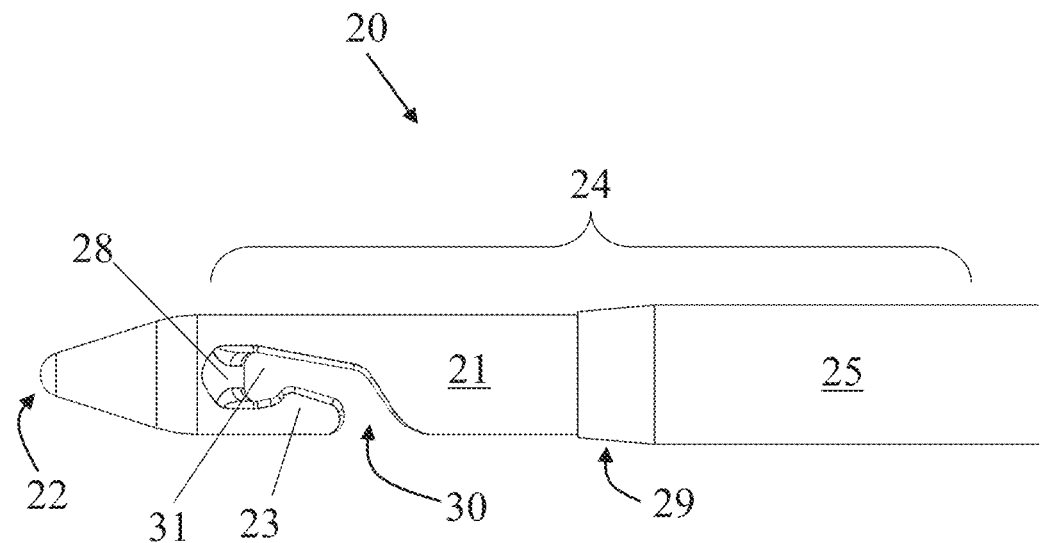
Figure 6D:
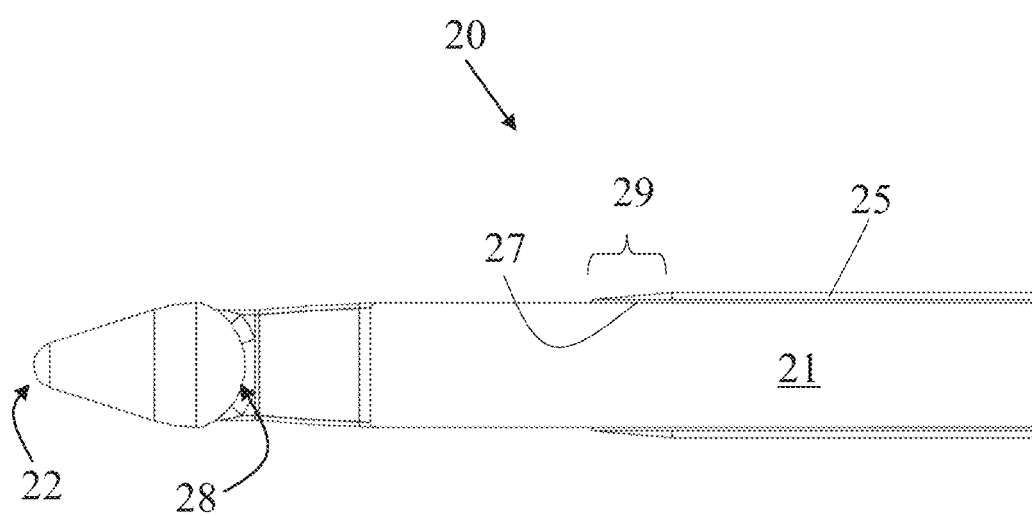

FIGS. 6A-6D illustrate views of an exemplary surgical tunneler and guidewire manipulator 20 that is configured to perform or facilitate selective execution of at least one, optionally at least two, or optionally at least three of the following exemplary steps: to form a surgical tunnel and part of a final insertion route, to engage and connect (e.g., hook and/or lock) to a target portion of a guidewire located inside a body of a subject, within or below subcutis thereof, to fixedly deform the guidewire to form a local deviated portion at or adjacent to the target portion, to fold an inner portion (e.g., the deviated portion) of the guidewire into a loop, and to reroute the guidewire from within the body by pulling the guidewire (e.g., at the loop, the deviated portion or the target portion) along the final insertion route. FIG. 6A shows a side of view of entire guidewire manipulator 20, FIG. 6B shows a side view of a distal portion of guidewire manipulator 20, FIG. 6C shows a top view of the distal portion of guidewire manipulator 20, and FIG. 6D shows a side cross sectional view of the distal portion of guidewire manipulator 20.

Guidewire manipulator 20 includes a rigid elongated body 21 optionally shapeable to a fixed chosen contour, having a cone-like end comprising a rounded or pointed distal tip 22 configured to dissect between tissue layers and/or to form a surgical tunnel when pushed subcutaneously in a body of a subject, for example. Guidewire manipulator 20 also includes a hook-shaped guidewire-capturing portion 23, provided proximally adjacent to distal tip 22, configured to capture or fasten to a target portion of a guidewire such that the guidewire can be folded and/or withdrawn from the target portion when drawn by guidewire manipulator 20 when guidewire capturing portion 23 engages the target portion. Guidewire capturing portion 23 forms an opening or slot 30 with juxtaposing proximal portion of elongated body 21 into an elongated body recess 31 sized to accommodate a length of guidewire (e.g., guidewire 11) extending across it.

Guidewire manipulator 20 also includes a guidewire deforming mechanism 24 configured to fasten and lock a guidewire target portion captured by guidewire capturing portion 23, and/or to fixedly deform the guidewire sufficiently to form a local deviated portion having reduces resistance to bending or folding relative to portions of the guidewire adjacent thereto. Guidewire deforming mechanism 24 includes a tubular member 25 selectively slidable axially over elongated body 21 and connected with proximal portion thereof to a manually operable trigger 26, such that tubular member 25 advances distally in accordance with travel length of the pressed trigger 26 up to a predetermined maximal travel length. Guidewire deforming mechanism 24 also includes a pressing portion 27 (e.g., a punch) configured to press against an anvil portion 28 (e.g., a die). Optionally and as shown, pressing portion 27 is part of tubular member 25 and located at or adjacent to a distal end thereof, whereas anvil portion 28 is part of elongated body 21 and located adjacent to guidewire capturing portion 23 in elongated body recess 31. In some embodiments, tubular member 25 includes a deformable portion 29 (which comprises distal end of tubular member 25) that is configured to conform and/or deform fixedly or elastically, at least partially, to and over the chosen shape imposed by the captured guidewire portion, when pressed by pressing portion 27 against anvil portion 28.

Anvil portion 28 and/or pressing portion 27 is optionally configured to form a chosen shape when pressing the guidewire target portion therebetween, the chosen shape may include a V-shape or a U-shape. Anvil portion 28 is optionally designed to facilitate and/or allow a predetermined minimal bend radius that prevents the captured guidewire target portion from reaching failure (e.g., breaking or disintegrating, at least in part). The anvil radius is optionally configured according to a chosen U-shape having a bend radius (i.e., an inside bend radius) which greater than the radius of the guidewire target portion. The bend radius is optionally at least two (2) times, optionally at least three (3) times, optionally at least five (5) times, the radius of the captured guidewire target portion. In some embodiments, guidewire deforming mechanism 24 is configured such that tubular member 25 can advance by a predetermined maximal travel by which pressing portion 27 moves across anvil portion 28 no less than the anvil radius in order to bend the wire to a bend angle (i.e., the angle through which the material is bent) being at least 90°, or optionally by at least 150°, or optionally by at least 180°, or optionally by at least 220°.

Figure 7A:
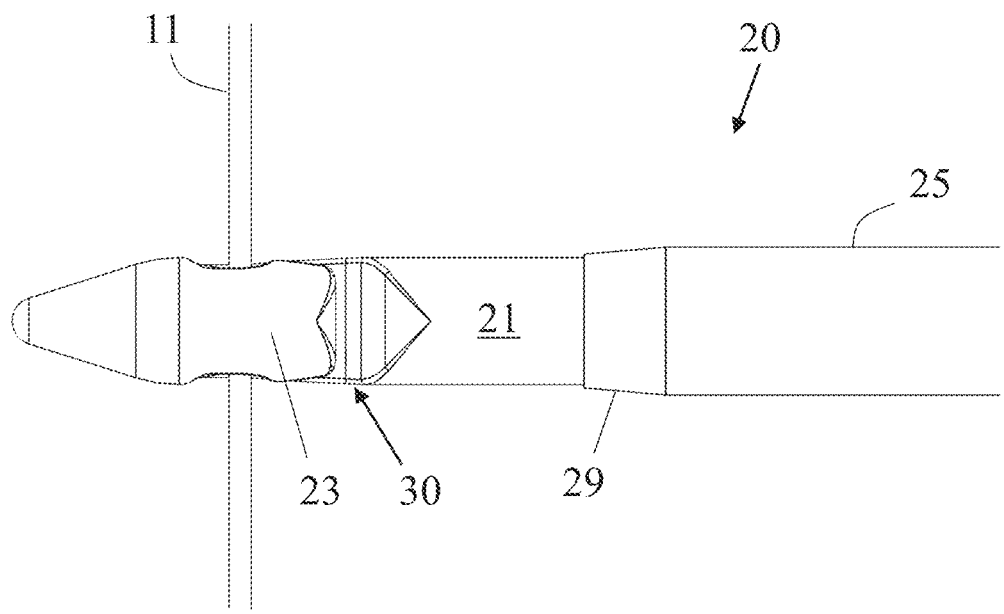
FIGS. 7A-7C schematically illustrate an exemplary sequence for fixedly deforming a guidewire using the guidewire manipulator shown in FIG. 6A, according to some embodiments.
Figure 7A:
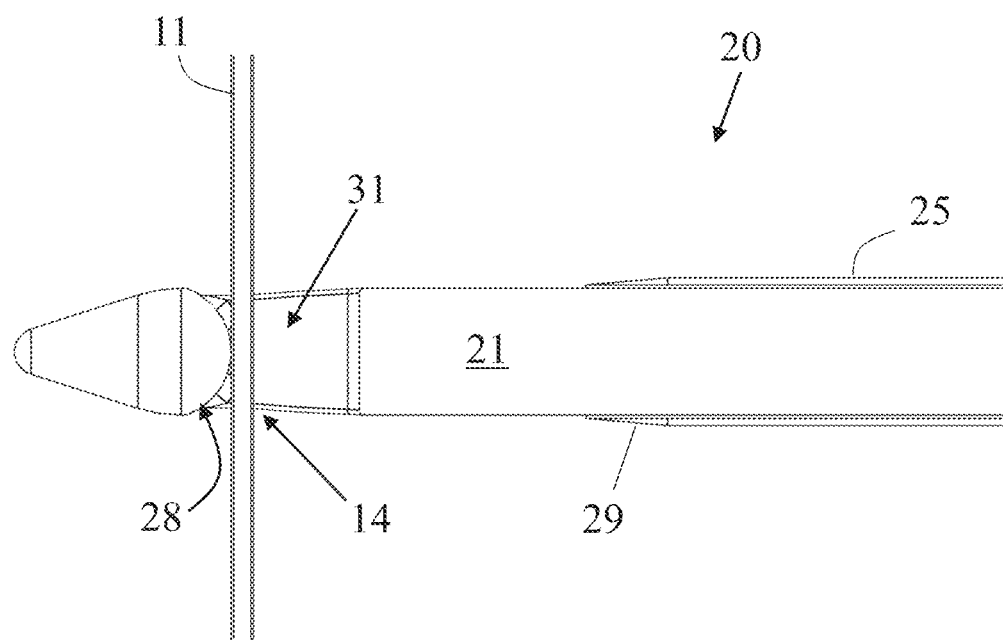
Figure 7B:
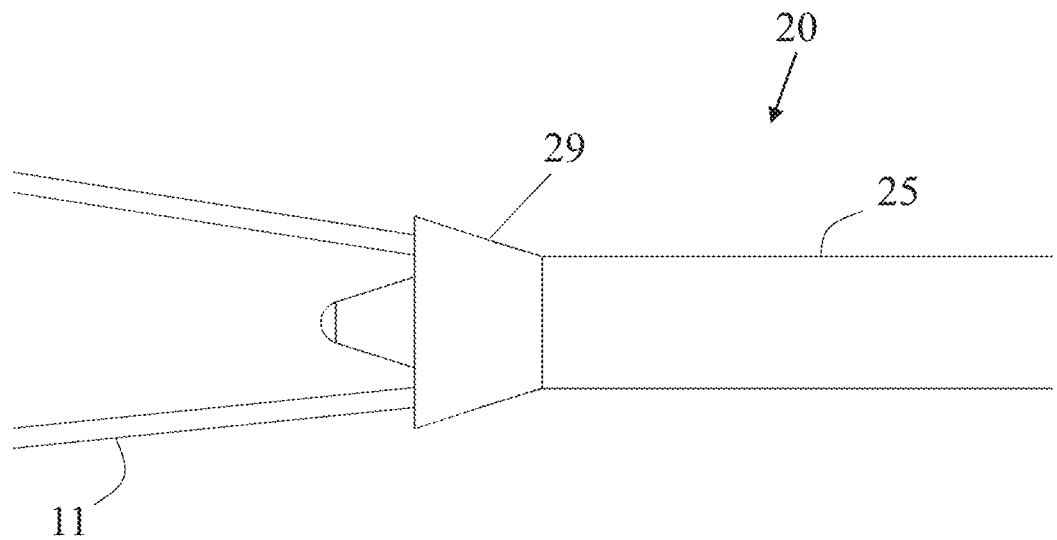
Figure 7B:
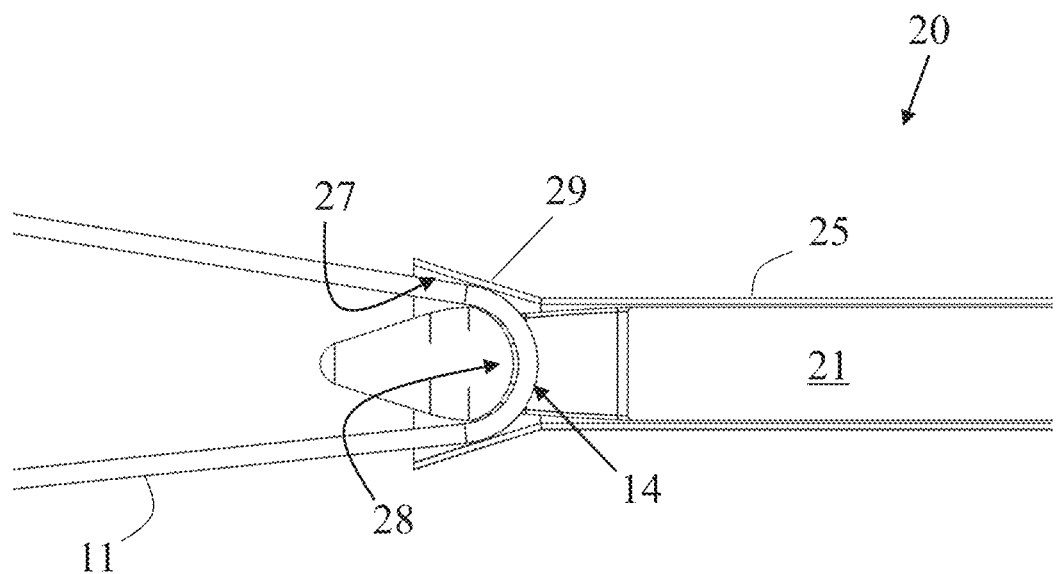
Figure 7C:
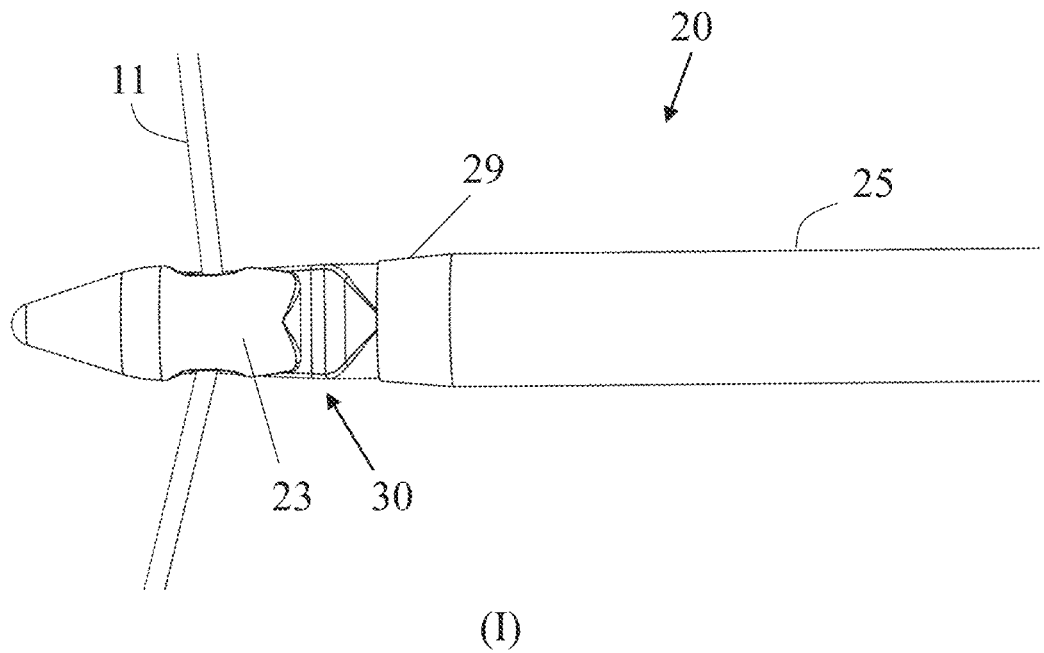
Figure 7C:
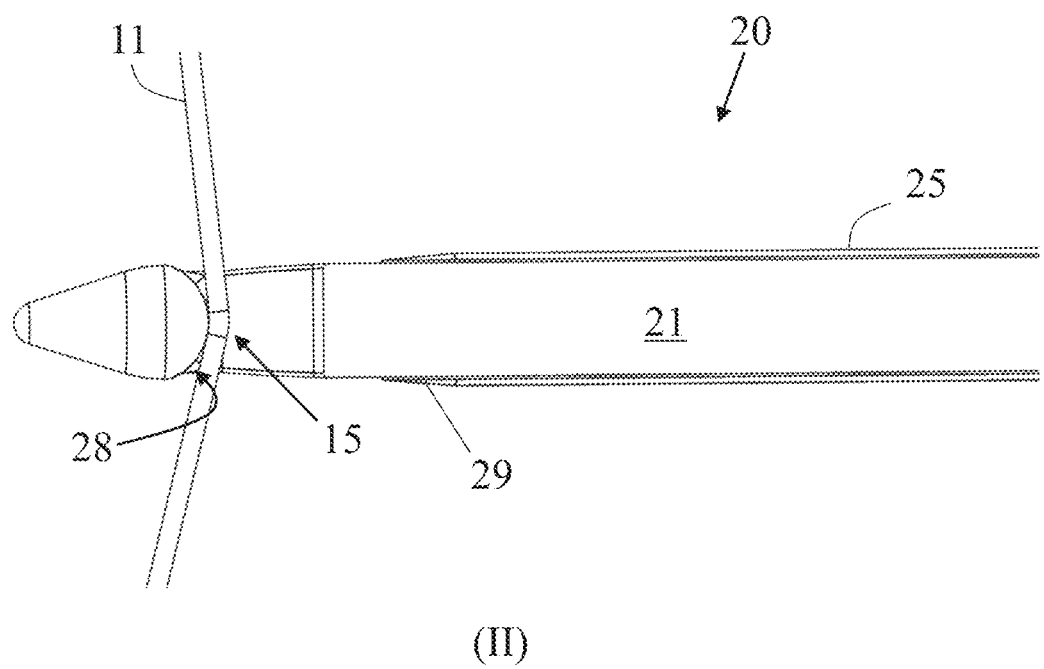

FIGS. 7A-7C schematically illustrate an exemplary sequence for fixedly deforming guidewire 11 using guidewire manipulator 20. FIGS. 7A (I) and (II) show respectively a side view and a cross sectional side view of the distal portion of guidewire manipulator 20 when engaging guidewire 11 adjacent to target portion 14 thereof. FIGS. 7B (I) and (II) show respectively a side view and a cross sectional side view of the distal portion of guidewire manipulator 20 when deforming guidewire 11. FIGS. 7C (I) and (II) show respectively a side view and a cross sectional side view of the distal portion of guidewire manipulator 20 following deforming and after releasing fixedly deviated portion 15 of guidewire 11. As shown in FIG. 7A, guidewire 11 is entrapped in elongated body recess 31 following lateral or transverse motion of guidewire manipulator 20 towards target portion 14 such that guidewire 11 passes into recess 31 through slot 30, then guidewire manipulator can be slightly pulled back such that guidewire target portion 14 is located inside recess 31 adjacent to guidewire capturing portion 23 and to anvil portion 28. FIG. 7B show compression of target portion 14 between pressing portion 27 and anvil portion 28, wherein target portion 14 deforms to a chosen shape defined by anvil portion 27, optionally comprising about 180° bending with a bending radius of no less than 3 times than the radius of target portion 14, while deformable portion 29 of tubular member 25 conforms to the deformed guidewire 11. FIG. 7C show guidewire manipulator 20 following withdrawal of tubular member 25, and guidewire 11 following compression against anvil portion 28 which caused it to fixedly deform with deviated portion 15. In some embodiments, deviated portion 15 is optionally minimal for allowing unhindered passage thereon such as with an introducer (e.g., peel-apart sheath), and for avoiding risk of mechanical failure. In some such embodiments, deviated portion 15 is inclined to adjacent portion of guidewire 11 by less than 45°, optionally by less than 30°, optionally by less than 15°.

Figure 8A:
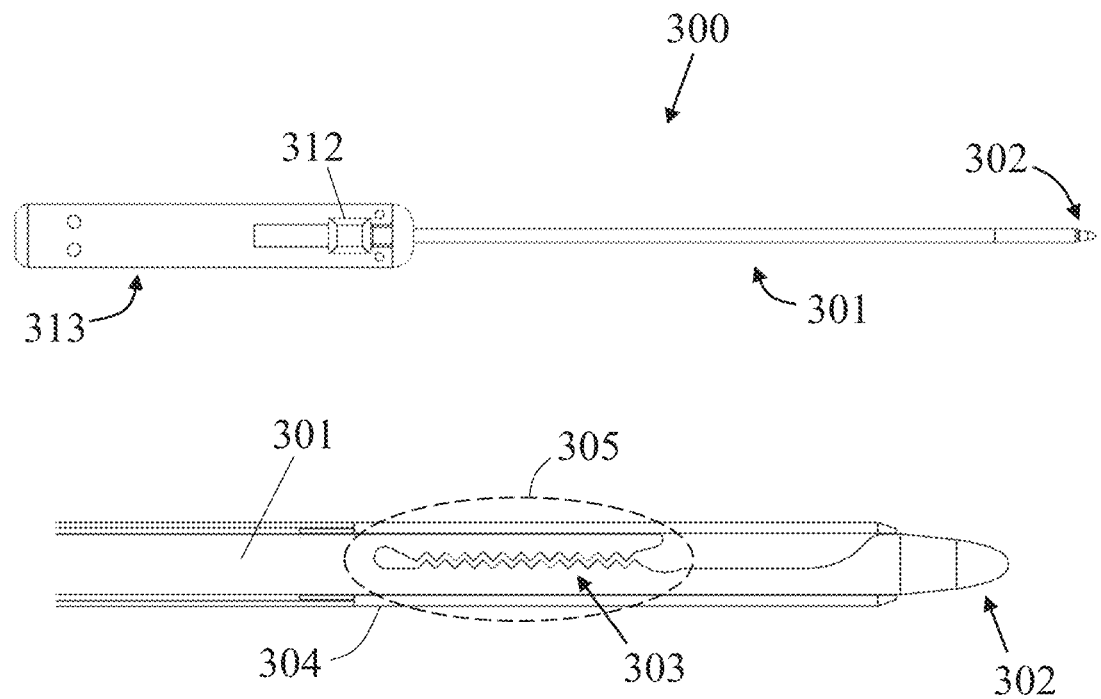
FIGS. 8A-8D illustrate views of an exemplary sequence for capturing and fastening onto a target portion of a guidewire using an exemplary surgical tunneler, according to some embodiments.
Figure 8B:
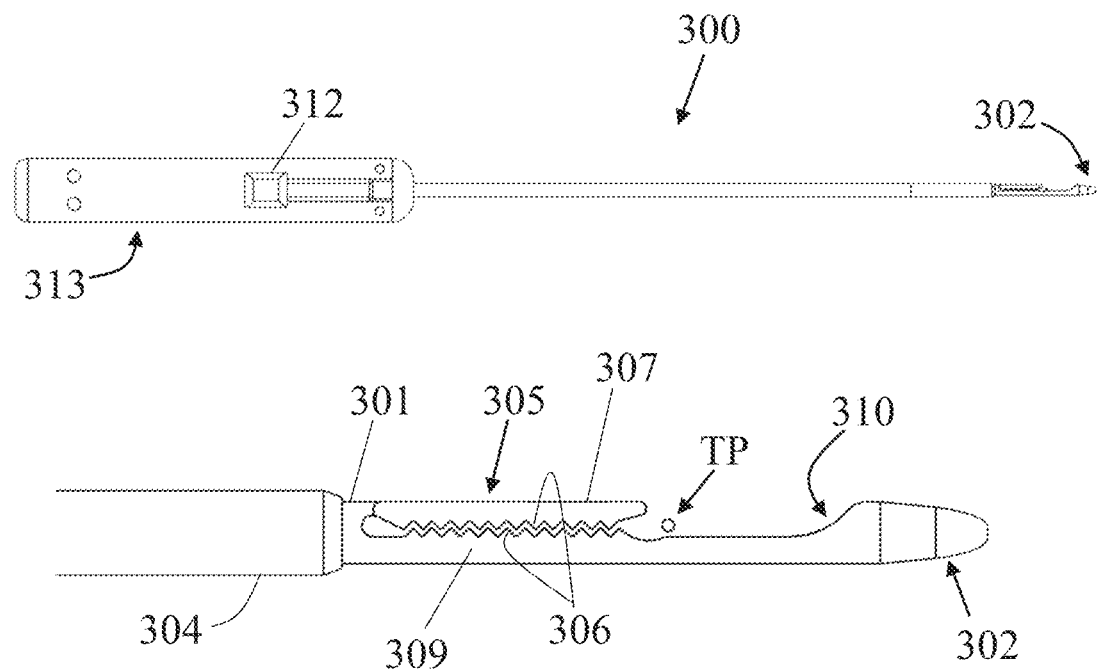
Figure 8C:
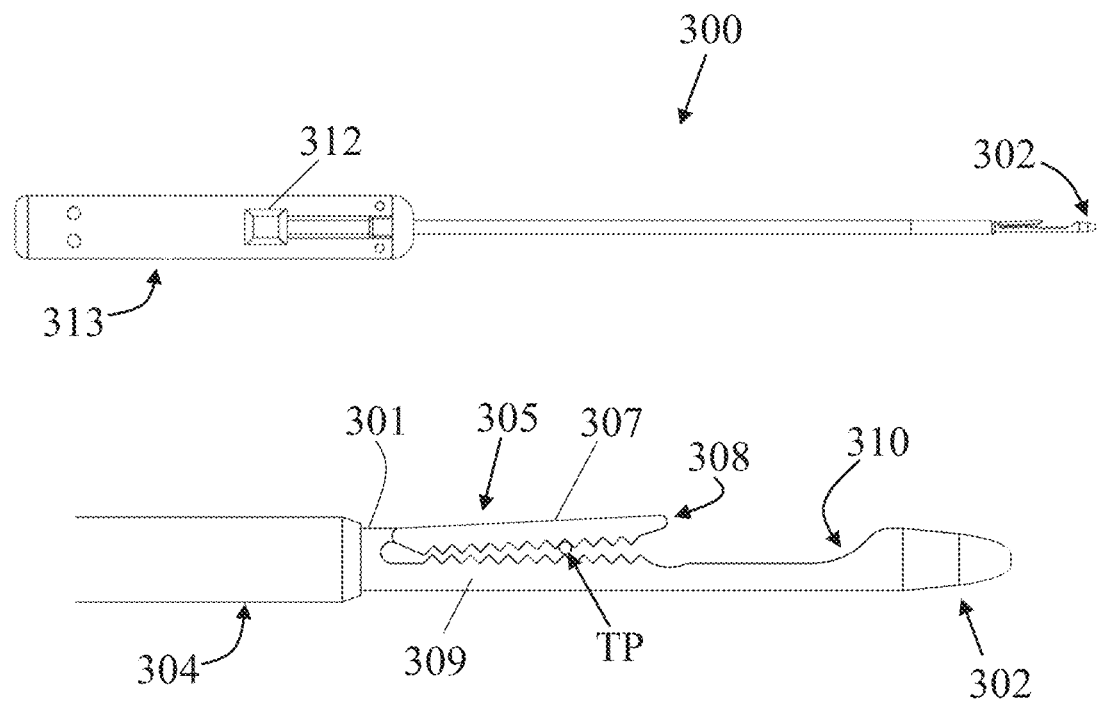
Figure 8D:
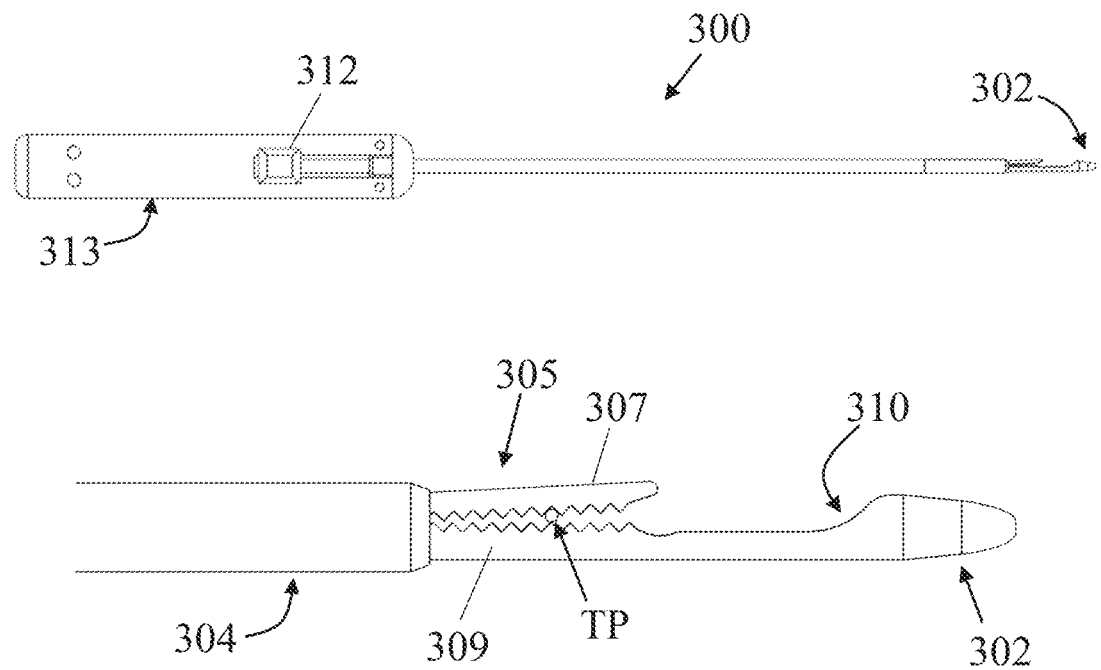

Reference is now made to FIGS. 8A-8D, which illustrate views of an exemplary sequence for capturing and fastening onto a target portion TP of a guidewire using an exemplary surgical tunneler 300. FIG. 8A illustrates a top view of surgical tunneler 300 and a cross sectional enlarged view of a distal portion thereof, when in a surgical tunneling configuration. FIG. 8B illustrates a top view of surgical tunneler 300 and an enlarged view of a distal portion thereof, when in a guidewire locating and capturing configuration before capturing the guidewire. FIG. 8C illustrates a top view of surgical tunneler 300 and an enlarged view of a distal portion thereof, when in the guidewire locating and capturing configuration after capturing the guidewire. FIG. 8D illustrates a top view of surgical tunneler 300 and an enlarged view of a distal portion thereof, when in a guidewire grasping and drawing configuration after capturing the guidewire. Surgical tunneler 300 is capable of locally manipulating, folding and/or fixedly deforming a chosen portion of an elastic stiff guidewire, when it is fastened onto target portion TP. It is important to note that elastic and stiff guidewires, unlike sutures or other highly flexible wires, are very difficult to manipulate or shape particularly small portions thereof, such as within a range of about 1 mm and about 20 mm. Elastic and stiff guidewires, used primarily to guide catheters or other tubular devices over them through bodily soft tissue and/or vasculature, commonly include a metal core with substantial resistance to bending along most of its length.

Surgical tunneler 300 includes a rigid elongated body 301, a rounded or pointed distal tip 302 and a guidewire capturing portion 303 provided proximally to distal tip 302. Distal tip 302 is configured to dissect between tissue layers and/or to form a surgical tunnel when pushed subcutaneously in the body. Guidewire capturing portion 303 is configured to capture and fasten onto target portion TP from within a body of a subject, such that the elastic stiff guidewire can be pulled and/or folded from the target portion, when drawn by surgical tunneler 300. Surgical tunneler 300 also includes a tubular member 304, which is selectively slidable axially over elongated body 301, between a distal-most position (as shown in FIG. 8A) wherein tubular member 304 covers guidewire capturing portion 303, and a proximal-most position (as shown in FIG. 8B) wherein guidewire capturing portion 303 is fully uncovered—for allowing capturing of target portion TP therewith. Tubular member 304 can be actuated to shift between the proximal-most and the distal-most position, or to other positions in-between, using knob 312 that is located on a handle 313 holding the proximal end of elongated body 301.

Surgical tunneler 300 includes a clip mechanism 305 incorporating guidewire capturing portion 303 (i.e., clip mechanism 305 is or includes guidewire capturing portion 303, or guidewire capturing portion 303 includes clip mechanism 305). Clip mechanism 305 includes a pair of opposing surfaces 306, which are optionally serrated, configured to capture and/or fasten onto target portion TP therebetween. Clip mechanism 305 includes a jaw portion 307 extending with a free end 308 thereof between elongated body 301 and distal tip 302. In some embodiments and as shown, jaw portion 307 emerges and/or protrudes distally from (or as part of) elongated body 301 with free end 308 towards distal tip 302. This configuration facilitates capturing of target portion TP by pushing pair of opposing surfaces 306 distally against target portion TP, optionally followed by pulling thereof for releasing any potential soft tissue entrapped by clip mechanism 305 (while holding target portion TP). In some embodiments, jaw portion 307 is sufficiently to bend and/or flex about one or more points thereof, such that free end 308 thereof can shift transversely (e.g., laterally) inwardly and/or outwardly relative to elongated body 301 and long axis thereof.

Jaw portion 307 extends in juxtaposition (optionally substantially parallel) with a stationary portion 309 of surgical tunneler 300. Stationary portion 309 extends from elongated body 301 to distal tip 302, such that it rigidly interconnects them as a unitary rigid body or structure sufficiently for forming a surgical tunnels and maneuver and/or deform target portion TP without yielding under stress. In some embodiments, elongated body 301, distal tip 302, stationary portion 309 and optionally jaw portion 307 are formed from (and as) a single unitary body or structure, and optionally clip mechanism 305 with jaw portion 307 and/or stationary portion 309 are formed by way of subtractive manufacturing, for example. Stationary portion 309 merges to distal tip 302 with a sloped surface 310 that is optionally configured for facilitating unhindered sliding of target portion TP towards clip mechanism 305 (as shown in FIG. 8B, for example).

In some embodiments, pair of opposing surfaces 306 is formed by and between jaw portion 307 and stationary portion 309, such that one surface of pair 306 is a portion of a surface of jaw portion 307 provided in front the other surface of pair 306 that is a portion of a surface of stationary portion 309. Clip mechanism 305 is configured to form a gap between pair of opposing surfaces 306, which is sized or sizable (optionally selectively) for allowing sliding and/or capturing of target portion TP between the surfaces of pair 306. In some embodiments, when clip mechanism 305 is in an elastically relaxed configuration, it is configured to form a gap between pair of opposing surfaces 306 smaller than a thickness of target portion TP, such that target portion TP will force pair of opposing surfaces 306 to widen the gap when target portion TP is captured therebetween (as shown in FIG. 8C, for example).

Tubular member 304 is selectively slidable axially over clip mechanism 305 (as shown in FIG. 8D for example), thereby forcing pair of opposing surfaces 306 to approximate with each other for fastening onto target portion TP. As such, when guidewire capturing portion 303 captures (e.g., engages with and/or holds) target portion TP, tubular member 304 is selectively shiftable distally from the proximal-most position until causing guidewire capturing portion 303 to fasten onto target portion TP. In some exemplary embodiments, after guidewire capturing portion 303 captures target portion TP, tubular member 304 can be shiftable distally from the proximal-most position until engaging with and causing the guidewire to fixedly deform sufficiently to form a local deviated portion, at or adjacent to target portion TP. In some embodiments, surgical tunneler 300 is configured to cause the guidewire to fixedly deform, such that the local deviated portion of the guidewire has smaller resistance to bending or folding relative to portions of the guidewire adjacent thereto.

Surgical tunneler 300 is configured for assisting in methods of implanting catheters or access lines along chosen surgical (e.g., subcutaneous) delivery and/or implantation routes, and it can be used for forming a subcutaneous surgical tunnel, for locating and/or capturing a target portion of elastic stiff guidewire within a body of a live subject via the surgical tunnel, to fasten (e.g., lock or grasp) onto the guidewire target portion or adjacent thereto, to manipulate and/or deform the guidewire via the its grasped target portion, and to withdraw and reroute the guidewire into the surgical tunnel by first pulling the target portion, as shown and described with respect to FIGS. 5A-5N for example.

In some embodiments, the guidewire is first extended along a preliminary insertion route within the body, between a first location on a skin of the subject and a bodily lumen, wherein a proximal end of the guidewire is outside the body and a distal end of the guidewire is inside the bodily lumen. Then a target portion (e.g., target portion TP) of the guidewire can be captured inside the body using surgical tunneler 300 (optionally followed by fastening onto the target portion), and then pulled with it to a second location on the skin, remote from the first location, wherein the guidewire follows a final insertion route within the body between the second location and the bodily lumen. An access line (e.g., vascular access line 100, for example) can then be delivered and implanted in the body along the final insertion route.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A surgical tunneler, comprising:
a rigid elongated body;
a handle at a proximal end of the rigid elongated body;
a user controllable actuator associated with the handle;

a rounded or pointed distal tip configured to dissect between tissue layers and/or to form a surgical tunnel when pushed subcutaneously in the body with the handle;

a guidewire capturing portion provided proximally to the distal tip configured to capture a target portion of an elastic stiff guidewire previously positioned at a subcutaneous location within a body of a subject by moving the guidewire capturing portion within a subcutaneous tunnel with the handle;

a guidewire fastening portion provided proximally to the distal tip and coupled to the actuator configured to fasten the target portion of the elastic stiff guidewire to the surgical tunneler when captured by the guidewire capturing portion at the subcutaneous location under control of the actuator;

wherein the guidewire can be drawn through the subcutaneous tunnel with the surgical tunneler by way of pulling from the target portion thereof when captured by and fastened to the surgical tunneler; and wherein the guidewire fastening portion of the surgical tunneler is capable of locally manipulating, folding and/or fixedly deforming a chosen portion of the elastic stiff guidewire, when the guidewire fastening portion fastens the target portion to the surgical tunneler;

wherein the guidewire capturing portion comprises a hook;

wherein the guidewire fastening portion comprises a tubular member selectively slidable axially over the rigid elongated body and the hook; and wherein the hook and the tubular member are configured to locally bend the elastic stiff guidewire when the target portion of the elastic stiff guidewire is captured within the hook.

2. The surgical tunneler according to claim 1, wherein the tubular member is selectively slidable between a distal-most position wherein the tubular member covers the guidewire capturing portion and a proximal-most position wherein the guidewire capturing portion is fully uncovered for allowing capturing of the target portion therewith.

3. The surgical tunneler according to claim 2, configured such that, when the guidewire capturing portion captures the target portion, the tubular member is selectively shiftable distally from the proximal-most position until causing the guidewire capturing portion to fasten onto the target portion.

4. The surgical tunneler according to claim 2, configured such that, when the guidewire capturing portion captures the target portion, the tubular member is selectively shiftable distally from the proximal-most position until engaging with and causing the guidewire to fixedly deform sufficiently to form a local deviated portion, at or adjacent to the target portion, having smaller resistance to bending or folding relative to portions of the guidewire adjacent thereto.

5. The surgical tunneler according to claim 1, comprising a guidewire deforming mechanism comprising an anvil portion at a base of the hook and a pressing portion at a distal end of the tubular member selectively movable one against the other and configured to press the guidewire therebetween to a chosen shape for fixedly deforming the guidewire and/or forming a local deviated portion.

6. The surgical tunneler according to claim 1, comprising a clip mechanism incorporating the guidewire capturing portion, the clip mechanism includes a pair of opposing surfaces configured to capture and/or fasten onto the target portion therebetween.

7. The surgical tunneler according to claim 6, wherein the clip mechanism comprises a jaw portion extending with a free end thereof between the rigid elongated body and the distal tip, in juxtaposition with a stationary portion extending from the rigid elongated body to the distal tip, wherein the pair of opposing surfaces is formed by and between the jaw portion and the stationary portion.

8. The surgical tunneler according to claim 7, wherein the jaw portion emerges and protrudes distally from the rigid elongated body with the free end thereof pointing towards the distal tip, so as to facilitate capturing of the target portion by pushing the pair of opposing surfaces distally against the target portion.

9. The surgical tunneler according to claim 7, wherein the stationary portion merges to the distal tip with a sloped surface configured for facilitating unhindered sliding of the target portion towards the clip mechanism.

10. The surgical tunneler according to claim 6, wherein the clip mechanism is configured to form a gap between the pair of opposing surfaces sized for allowing sliding and/or capturing of the target portion therebetween.

11. The surgical tunneler according to claim 10, further comprising a tubular member selectively slidable axially over the clip mechanism, thereby forcing the pair of opposing surfaces to approximate for fasten onto the target portion.

12. The surgical tunneler according to claim 6, wherein the clip mechanism, when in an elastically relaxed configuration, is configured to form a gap between the pair of opposing surfaces smaller than a thickness of the target portion, such that the target portion forces the pair of opposing surfaces to widen the gap when captured therebetween.

13. The surgical tunneler according to claim 6, wherein the pair of surfaces are serrated.

14. The surgical tunneler according to claim 1, wherein the guidewire capturing portion is configured as a carabiner comprising an elastically swingable gate shiftable laterally from a closed state towards a recess formed in the elongated body, when the gate is pressed against the target portion, and to elastically swing back to the closed state when the target portion extends through the recess and disengages from the gate.

15. The surgical tunneler according to claim 14, comprising a tissue cutting portion extending adjacent and/or parallel to the guidewire capturing carabiner, configured to cut through soft tissue between the guidewire capturing carabiner and the target portion.

16. The surgical tunneler according to claim 15, wherein the tissue cutting portion includes a blade and/or cutting teeth.

17. The surgical tunneler according to claim 15, wherein the tissue cutting portion extends along a length of the gate.

18. The surgical tunneler according to claim 13, wherein the rigid elongated body is shapeable to a fixed chosen contour.

19. A kit comprising:
a surgical tunneler comprising:
a rigid elongated body;
a handle at a proximal end of the rigid elongated body;
a user controllable actuator associated with the handle;
a rounded or pointed distal tip configured to dissect between tissue layers and/or to form a surgical tunnel when pushed subcutaneously in the body with the handle;
a guidewire capturing portion provided proximally to the distal tip configured to capture a target portion of an elastic stiff guidewire previously positioned at a subcutaneous location within a body of a subject by moving the guidewire capturing portion within a subcutaneous tunnel with the handle;

a guidewire fastening portion provided proximally to the distal tip and coupled to the actuator configured to fasten the target portion of the elastic stiff guidewire to the surgical tunneler when captured by the guidewire capturing portion at the subcutaneous location under control of the actuator;

wherein the guidewire can be drawn through the subcutaneous tunnel with the surgical tunneler by way of pulling from the target portion thereof when captured by and fastened to the surgical tunneler; and wherein the guidewire fastening portion of the surgical tunneler is capable of locally manipulating, folding and/or fixedly deforming a chosen portion of the elastic stiff guidewire, when guidewire fastening portion fastens the target portion to the surgical tunneler;

wherein the guidewire capturing portion comprises a hook;

wherein the guidewire fastening portion comprises a tubular member selectively slidable axially over the rigid elongated body;

wherein the hook and the tubular member are configured to locally bend the elastic stiff guidewire when the target portion of the elastic stiff guidewire is captured within the hook; and at least one of a guidewire, an introducer, and a vascular access line.

20. The kit according to claim 19 comprising the introducer, wherein the introducer comprises a splittable sheath placed over a dilator, configured to pass over the guidewire and to allow passing of the vascular access line therethrough.

21. The kit according to claim 19 comprising the vascular access line, wherein the vascular access line comprises:
a distal portion configured for placement in a blood vessel in a body of a subject;
an intermediate portion configured to pass through a surgical opening and extend across skin layers in the body;
a proximal portion configured to reside outside the body; and
an elevating member fixedly attachable to the body, comprising an elevated channel provided at a chosen height relative to a bottom surface of the elevating member;
wherein the elevating member is configured to accommodate and/or hold the proximal portion within the elevated channel in a chosen shaped route above the bottom surface, when the elevating member is fixedly attached to the body, such that the intermediate portion is fixed at a chosen angle relative to the bottom surface and/or the blood vessel when in elastically relaxed state.

22. The kit according to claim 21, wherein the shaped route is curved and comprising an apex pointing away from or towards the bottom surface.

23. The kit according to claim 21, wherein the elevating member is attachable to the body by way of adhesion and/or suturing to an outer skin surface of the body.

24. The kit according to claim 21, wherein the elevating member is configured as a catheter hub and is fixedly connected to the proximal portion such as by way of overmolding.

25. The kit according to claim 21, wherein the elevating member is releasably or permanently connectable to a catheter hub fixedly connected to and/or molded over the proximal portion.

26. The kit according to claim 21, wherein the chosen angle is within a range of 20° to 90°, optionally about 45°.

27. The kit according to claim 21, wherein the vascular access line comprises two juxtaposing lumens, wherein the proximal portion includes a merging section, wherein the two juxtaposing lumens are divided between two distinct bodies extending proximally to the merging section, and divided by a wall in a unitary body extending distally to the merging section.

28. The kit according to claim 21, wherein the distal portion includes a first bent or curved section configured with a first radius of curvature and a first curve length when in an elastically relaxed state.

29. The kit according to claim 28, wherein the first bent or curved section is bent or curved upwards towards a plane coinciding with the bottom surface.

30. The kit according to claim 28, wherein the distal portion includes a second bent or curved section configured with a second radius of curvature and a second curve length when in an elastically relaxed state.

31. The kit according to claim 30, wherein the second bent or curved section is bent or curved downwards away from a plane coinciding with the bottom surface.

32. A surgical tunneler, comprising:
a rigid elongated body;
a handle at a proximal end of the rigid elongated body;
a user controllable actuator associated with the handle;
a rounded or pointed distal tip configured to dissect between tissue layers and/or to form a surgical tunnel when pushed subcutaneously in the body with the handle;
a hook provided on a distal portion of the rigid elongated body proximally to the distal tip, wherein the hook is configured to capture a target portion of an elastic stiff guidewire previously positioned within a body of a subject by moving the hook within the body of the subject with the handle; and
a slidable sleeve provided around the rigid elongated body and coupled to the actuator, wherein the slidable sleeve is configured under control of the actuator to fasten the target portion of the elastic stiff guidewire within the hook;
wherein the hook and the slidable sleeve are configured to locally bend the elastic stiff guidewire when the target portion of the elastic stiff guidewire is captured within the hook.

33. The surgical tunneler of claim 32, wherein the hook comprises an anvil with a curved surface at a base of the hook.

34. The surgical tunneler of claim 33, wherein the slidable sleeve is configured to bend the target portion of the elastic stiff guidewire over the curved surface of the anvil at the base of the fixed hook, wherein the guidewire can be drawn with the surgical tunneler by way of pulling from the target portion thereof.

* * * * *